United States Patent [19]

Karanewsky

[11] Patent Number: 5,189,180

[45] Date of Patent: Feb. 23, 1993

[54] SECO-MEVINIC ACID DERIVATIVES USEFUL AS ANTIHYPERCHOLESTEROLEMIC AGENTS AND NEW INTERMEDIATES

[75] Inventor: Donald S. Karanewsky, Robbinsville, N.J.

[73] Assignee: E. R. Squibb & Sons, Inc., Princeton, N.J.

[21] Appl. No.: 694,515

[22] Filed: May 1, 1991

Related U.S. Application Data

[62] Division of Ser. No. 413,656, Sep. 28, 1989, Pat. No. 5,025,017.

[51] Int. Cl.$^5$ ................ C07D 311/02; C07D 319/06; C07F 7/02; C07F 7/08
[52] U.S. Cl. ..................... 549/214; 549/283; 549/290; 549/374; 549/375; 549/369; 549/370; 549/60; 549/373; 556/440; 544/60; 544/148; 544/374; 544/336; 544/335; 540/575; 546/152; 546/176; 546/181; 546/207; 546/268; 548/203; 548/204; 548/517; 548/311.1; 548/335.1; 548/214; 548/247; 548/335.5
[58] Field of Search ................ 549/214; 560/255; 556/440

[56] References Cited

U.S. PATENT DOCUMENTS

| | | | |
|---|---|---|---|
| 3,983,140 | 9/1976 | Endo et al. | 549/292 |
| 4,049,495 | 9/1977 | Endo et al. | 435/125 |
| 4,137,322 | 1/1979 | Endo et al. | 560/119 |
| 4,375,475 | 3/1983 | Willard et al. | 549/292 |
| 4,873,345 | 10/1989 | Duggan | 549/214 |
| 5,025,017 | 6/1991 | Karanewsky | 549/214 |

FOREIGN PATENT DOCUMENTS

| | | |
|---|---|---|
| 0142146A2 | 7/1988 | European Pat. Off. . |
| 0186973 | 10/1984 | Japan . |
| 8603488 | 11/1985 | PCT Int'l Appl. . |
| 1586152 | 5/1978 | United Kingdom . |

OTHER PUBLICATIONS

Tetrahedron Letters, vol. 29, No. 8, 929-930, 1988.
C. H. Heathcock et al, "Synthesis and Biological Evaluation of a Monocyclic, Fully Functional Analogue of Compactin," J. Med. Chem. 1989, 32, 197.

*Primary Examiner*—C. Warren Ivy
*Assistant Examiner*—A. Owens
*Attorney, Agent, or Firm*—Burton Rodney

[57] ABSTRACT

Seco-mevinic acid derivatives are provided which have the structure

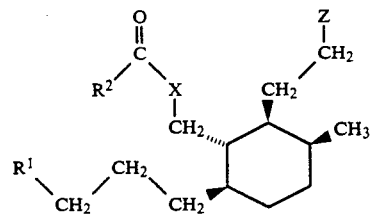

including all stereoisomers thereof, wherein Z is

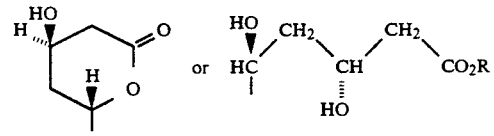

R is H, alkali metal or lower alkyl, $R^1$ is H, lower alkyl, aryl, lower alkoxy, cycloalkyl, heteroaryl, aralkyl, heteroaralkyl or heterocyclic; $R^2$ is lower alkyl, cycloalkyl or aralkyl, and X is O or $NR^5$ wherein $R^5$ is H or lower alkyl, and are HMG CoA reductase inhibitors and thus are useful as antihypercholesterolemic agents and in treating atherosclerosis.

New intermediates for preparing the above seco-mevinic acid derivatives are also provided.

3 Claims, No Drawings

SECO-MEVINIC ACID DERIVATIVES USEFUL AS ANTIHYPERCHOLESTEROLEMIC AGENTS AND NEW INTERMEDIATES

This is a division of application Ser. No. 413,656, filed Sep. 28, 1989 now U.S. Pat. No. 5,025,017.

FIELD OF THE INVENTION

The present invention relates to secomevinic acid derivatives which are HMG CoA reductase inhibitors and thus are useful as antihypercholesterolemic agents and to new intermediates employed in preparing such compounds.

BACKGROUND OF THE INVENTION

F. M. Singer et al., "New Inhibitors of in vitro Conversion of Acetate and Mevalonate to Cholesterol", *Proc. Soc. Exper. Biol. Med.*, 102, 370 (1959) and F. H. Hulcher, "Inhibition of Hepatic Cholesterol Biosynthesis by 3,5-Dihydroxy-3,4,4,-trimethylvaleric Acid and its Site of Action," *Arch. Biochem. Biophys.*, 146, 422 (1971) disclose that certain mevalonate derivatives inhibit the biosynthesis of cholesterol.

Singer et al. reported that fluoromevalonic acid is more effective in inhibiting biosynthesis of cholesterol (as measured by in vitro conversion of labeled acetate and labeled mevalonate into cholesterol) than Δ4-androstene-17α-ol-3-one-17β-oic acid and Δ1-testololactone.

Hulcher reported that an analog of mevalonic acid, namely, 3,5-dihydroxy-3,4,4-trimethylvaleric acid strongly inhibits cholesterol biosynthesis by rat liver homogenates.

U.S. Pat. No. 3,983,140 to Endo et al. discloses the fermentation product ML-236B referred to generically as compactin

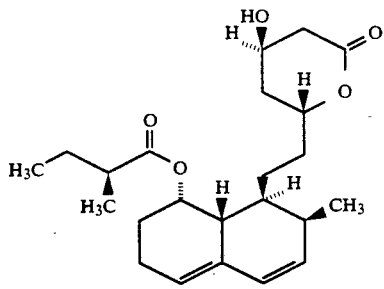

(also referred to as mevastatin) which is prepared by cultivation of a microorganism of the genus Penicillium. This fermentation process is disclosed in U.S. Pat. No. 4,049,495 issued Sep. 20, 1977 to Endo et al.

Brown, A. G., et al., (Beecham Pharmaceuticals Research Div.), "Crystal and Molecular Structure of Compactin, a New Antifungal Metabolite from Penicillium Brevicompactum", *J. Chem. Soc. Perkin I.* 1165–1170 (1976) confirms that compactin has a complex mevalonolactone structure as disclosed by Endo et al. in the above patents.

U.S. Pat. No. 4,231,938 to Monaghan et al. discloses mevinolin (lovastatin, Monacolin K)

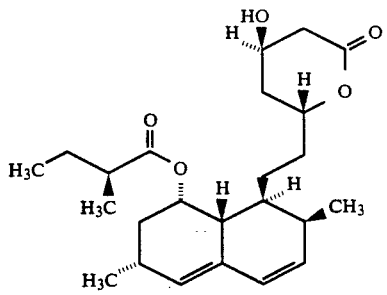

(also referred to as MK-803) which is prepared by culturing a microorganism of the genus Aspergillus.

U.S. Pat. No. 4,346,227 to Terahara et al discloses pravastatin

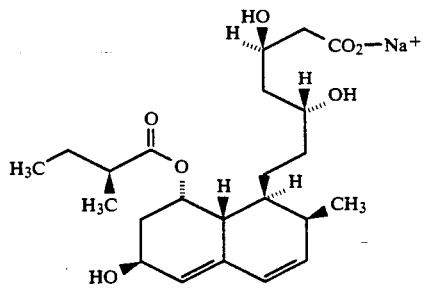

Pravastatin is prepared by the enzymatic hydroxylation of compactin or its carboxylic acid as disclosed in U.S. Pat. No. 4,410,629 to Terahara et al.

U.S. Pat. No. 4,448,979 issued May 15, 1984 to Terahara et al discloses the lactone of pravastatin.

U.S. Pat. Nos. 4,444,784 and 4,450,171 to Hoffman et al disclose various antihypercholesterolemic compounds including synvinolin (simvastatin)

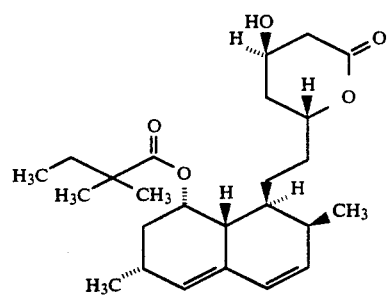

as well as compounds of the structures

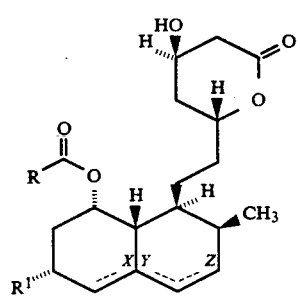

and

-continued

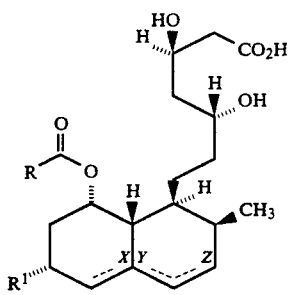

wherein $R^1$ is H or $CH_3$, R can be an alkyl group including

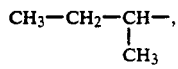

X, Y and Z are single and/or double bonds in all possible combinations.

European Patent Application 0065835A1 filed by Sankyo discloses cholesterol biosynthesis inhibiting compounds of the structure

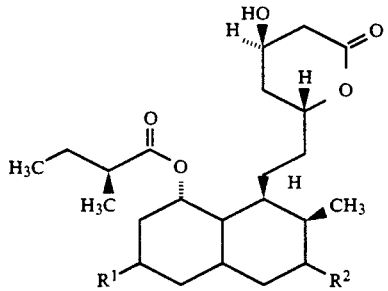

and their corresponding free carboxylic acids, which may be represented by the following formula

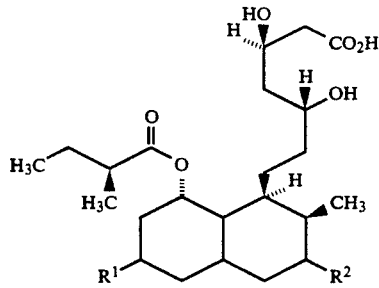

(in which one of $R^1$ and $R^2$ represents a hydrogen atom and the other represents a hydroxy group), and salts and esters of the carboxylic acids.

European Patent Application 0142146A2 filed by Merck discloses mevinolin-like compounds of the structure

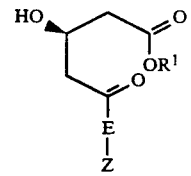

I.

wherein
$R^1$ is
1) hydrogen,
2) $C_{1-4}$alkyl
3) 2,3-dihydroxypropyl,
4) alkali metal cation, such as $Na^+$, or $K^+$, or
5) ammonium of formula $NR^3R^4R^5R^6$ wherein $R^3$, $R^4$, $R^5$ and $R^6$ are independently hydrogen or $C_{1-4}$alkyl or two of $R^3$, $R^4$, $R^5$ and $R^6$ are joined together to form a 5 or 6-membered heterocycle such as pyrrolidino or piperidino with the nitrogen to which thy are attached;

E is $-CH_2CH_2-$, $-CH=CH-$, or $-(CH_2)_3-$; and Z is

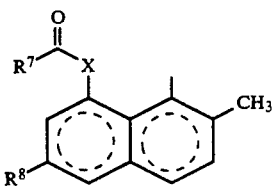

1)

wherein the dotted lines represent all of the possible oxidation states of the bicyclic system such as naphthalene, dihydro-, tetrahydro-, hexahydro-, octahydro-, and decahydronaphthalene;
X is $-O-$ or $NR^9$ wherein
$R^9$ is H or $C_{1-3}$alkyl;
$R^7$ is $C_{2-8}$alkyl; and
$R^8$ is H or $-CH_3$;

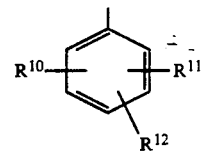

2)

wherein $R^{10}$, $R^{11}$ and $R^{12}$ are independently
a) hydrogen,
b) halogen, such as bromo, chloro or fluoro,
c) $C_{1-4}$alkyl,
d) halo-$C_{1-4}$alkyl,
e) phenyl either unsubstituted or substituted with one or more of
  i) $C_{1-4}$alkyl,
  ii) $C_{1-4}$alkyl,
  iii) $C_{2-8}$alkanoyloxy, or
  iv) halo-$C_{1-4}$alkyl,
  v) halo, such as bromo, chloro or fluoro,
f) $OR^{13}$ wherein $R^{13}$ is
  i) hydrogen,
  ii) $C_{1-8}$alkanoyl,
  iii) benzoyl,
  iv) phenyl,
  v) halophenyl, vi) phenyl-$C_{1-3}$alkyl, either unsubstituted or substituted with one or more halogen, $C_{1-4}$alkoxy, $C_{1-4}$alkyl or halo-$C_{1-4}$alkyl,
vii) $C_{1-9}$alkyl,
viii) cinnamyl,
ix) halo-$C_{1-4}$alkyl,
x) allyl,
xi) $C_{3-6}$cycloalkyl-$C_{1-3}$alkyl,
Xii) adamantyl-$C_{1-3}$alkyl,

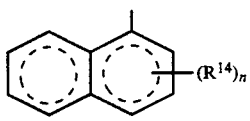

3)

wherein n is 0–2, and $R^{14}$ is halo such as chloro, bromo or fluoro, or $C_{1-4}$ alkyl, and

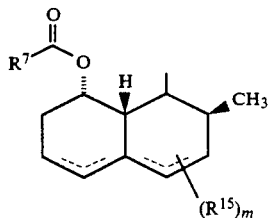

4)

wherein the dotted lines represent possible double bonds there being 0, 1 or 2 double bonds; m represents 1, 2 or 3; and $R^{15}$ is
1) methyl,
2) hydroxy,
3) $C_{1-4}$alkoxy,
4) oxo or
5) halo.

In the discussion of the prior art at pages 2 and 3 of the above European patent, it is indicated that HMG CoA reductase inhibitors reported in the patent literature and elsewhere include compactin; mevinolin, di- and tetrahydro derivatives thereof; analogs with different esters in the 8-position of the polyhydronaphthalene moiety, totally synthetic analogs, wherein the polyhydronaphthalene moiety is replaced by substituted mono- and bicyclic aromatics. The applicant states at pages 3 and 4 as follows:

"But in all instances the active compound included a 4-hydroxytetrahydropyran-2-one ring or the corresponding 3,5-dihydroxy acid, or derivatives thereof, formed by opening the pyranone ring such as:

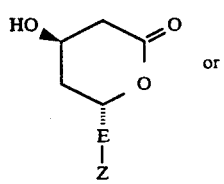

II or

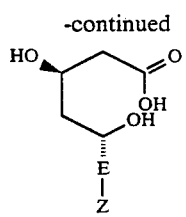

IIa

In all of these compounds the 3,5-dihydroxy acid or corresponding lactone moiety is present and the particular stereochemistry depicted is essential for manifestation of the optimum enzyme inhibitory activity."

GB 1,586,152 discloses a group of synthetic compounds of the formula

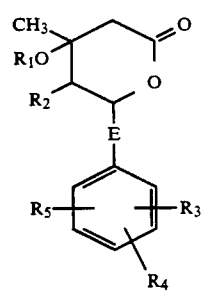

in which E represents a direct bond, a $C_{1-3}$ alkylene bridge or a vinylene bridge and the various R's represent a variety of substituents.

The activity reported in the U.K. patent is less than 1% that of compactin.

U.S. Pat. No. 4,375,475 to Willard et al discloses hypocholesterolemic and hypolipemic compounds having the structure

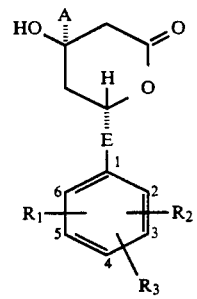

wherein A is H or methyl; E is a direct bond, —$CH_2$—, —$CH_2$—$CH_2$—, —$CH_2$—$CH_2$—$CH_2$— or —CH=CH—; $R_1$, $R_2$ and $R_3$ are each selected from H, halogen, $C_{1-4}$ alkyl, $C_{1-4}$ haloalkyl, phenyl, phenyl substituted by halogen, $C_{1-4}$ alkoxy, $C_{2-8}$ alkanoyloxy, $C_{1-4}$ alkyl, or $C_{1-4}$ haloalkyl, and $OR_4$ in which $R_4$ is H, $C_{2-8}$ alkanoyl, benzoyl, phenyl, halophenyl, phenyl $C_{1-3}$ alkyl, $C_{1-9}$ alkyl, cinnamyl, $C_{1-4}$ haloalkyl, allyl, cycloalkyl-$C_{1-3}$-alkyl, adamantyl-$C_{1-3}$-alkyl, or substituted phenyl $C_{1-3}$-alkyl in each of which the substituents are selected from halogen, $C_{1-4}$ alkoxy, $C_{1-4}$ alkyl, or $C_{1-4}$ haloalkyl; and the corresponding dihydroxy acids resulting from the hydrolytic opening of the lactone ring, and the pharmaceutically acceptable salts of said acids, and the $C_{1-3}$ alkyl and phenyl, dimethylamino or acetylamino substituted $C_{1-3}$-alkyl esters of the dihydroxy acids; all of the compounds being the enantiomers having a 4 R configuration in the tetrahydropyran moiety of the trans racemate shown in the above formula.

GB 2162-179-A discloses napthyl analogues of mevalolactone useful as cholesterol biosynthesis inhibitors having the structure

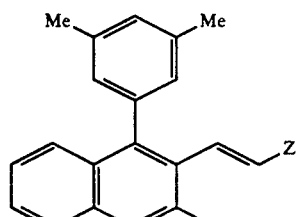

wherein $R_1 = 1$-3C alkyl;
Z is a gp. of formula $Z_1$ or $Z_2$:

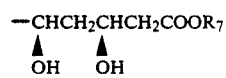

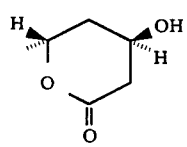

$R_7 = H$, a hydrolysable ester gp. or a cation.

European Patent No. 164-698-A discloses preparation of lactones useful as anti-hypercholesterolemic agents by treating an amide with an organic sulphonyl halide $R^5SO_2X$, then removing the protecting group Pr.

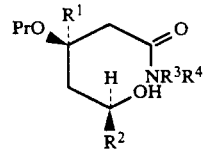

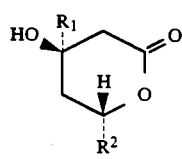

wherein
X = halo;
Pr = a carbinol-protecting group;
$R^1$ = H or $CH_3$;
$R^3$, $R^4$ = H, 1-3C alkyl or phenyl-(1-3C alkyl), the phenyl being optionally substituted by 1-3C alkyl, 1-3C alkoxy or halo;
$R^2$ = a group of formula (A) or (B):

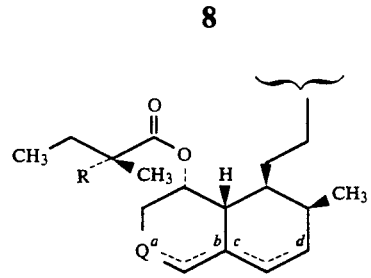

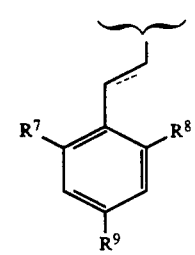

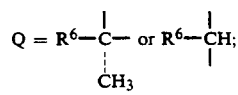

$R^6$ = H or OH;
R = H or $CH_3$;
a, b, c and d = optional double bonds;
$R^7$ = phenyl or benzyloxy, the ring in each case being optionally substituted by 1-3C alkyl or halo;
$R^8$, $R^9$ = 1-3C alkyl or halo;
$R^5$ = 1-3C alkyl, phenyl or mono- or di-(1-3C alkyl)-phenyl.

Anderson, Paul Leroy, Ger. Offen. DE 3,525,256 discloses naphthyl analogs of mevalonolactones of the structure

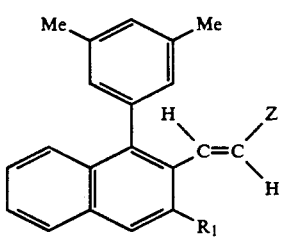

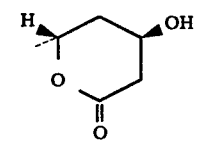

wherein $R^1$ is alkyl, Z=Q, $Q^1$; $R^7$=H, or a hydrolyzable ester group useful as inhibitors of cholesterol biosynthesis and in treatment of atherosclerosis.

WO 8402-903 (based on U.S. application Ser. No. 460,600, filed Jan. 24, 1983) filed in the name of Sandoz AG discloses mevalono-lactone analogues useful as hypolipoproteinaemic agents having the structure

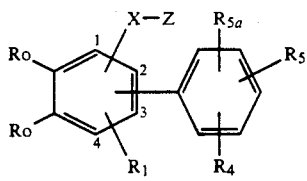

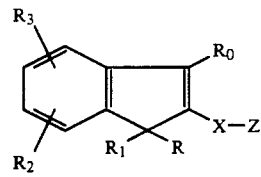

wherein the two groups Ro together form a radical of formula

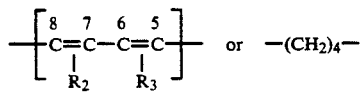

wherein R₂ is hydrogen, $C_{1-4}$ alkyl, $C_{1-4}$ alkoxy, (except t-butoxy), trifluoromethyl, fluoro, chloro, phenoxy or benzyloxy, R₃ is hydrogen, $C_{1-3}$ alkyl, $C_{1-3}$ alkoxy, trifluoromethyl, fluoro, chloro, phenoxy or benzyloxy, with the provisos that not more than one of R₂ and R₃ is trifluoromethyl, not more than one of R₂ and R₃ is phenoxy, and not more than one of R₂ and R₃ is benzyloxy, R₁ is hydrogen, $C_{1-6}$ alkyl, fluoro, chloro or benzyloxy, R₄ is hydrogen, $C_{1-4}$ alkyl, $C_{1-4}$ alkoxy, (except t-butoxy), trifluoromethyl, fluoro, chloro, phenoxy or benzyloxy, R₅ is hydrogen, $C_{1-3}$ alkyl, $C_{1-3}$ alkoxy, trifluoromethyl, fluoro, chloro, phenoxy or benzyloxy, R₅ₐ is hydrogen, $C_{1-2}$ alkyl, $C_{1-2}$ alkoxy, fluoro or chloro, and with the provisos that not more than one of R₄ and R₅ is trifluoromethyl, not more than one of R₄ and R₅ is phenoxy and not more than one of R₄ and R₅ is benzyloxy,

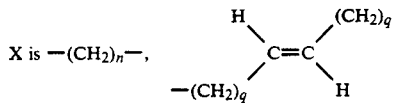

wherein n is 0, 1, 2 or 3 and both q's are 0 or one is 0 and the other is 1,

Z is

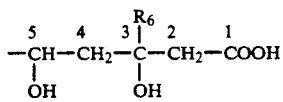

wherein R₆ is hydrogen or $C_{1-3}$ alkyl, with the general proviso that -X-Z and the R₄ bearing phenyl group are ortho to each other;

in free acid form or in the form of a physiologically-hydrolysable and acceptable ester or a 6 lactone thereof or in salt form.

WO 8603-488-A (Sandoz AG) discloses indene analogues of mevalolactone, useful as hypolipoproteinaemia and anti-atherosclerotic agents, in free acid form or in the form of an ester or delta-lactone or in salt form which have the formula R=H or primary or secondary 1-6C alkyl;
R₁ = primary or secondary 1-6C alkyl; or R+R₁ =(CH₂)ₘ or (Z)—CH₂—CH=CH—CH₂;
m=2-6;
Rₒ=1-6C alkyl, 3-7C cycloalkyl or R₄, R₅, R₆-substituted phenyl;
R₂, R₄=H, 1-4C alkyl, 1-4C alkoxy (except t-butoxy), CF₃, F, Cl, phenoxy or benzyloxy;
R₃ and R₅=H, 1-3C alkyl, 1-3C alkoxy, CF₃, F, Cl, phenoxy or benzyloxy;
R₆=H, 1-2C alkyl, 1-2C alkoxy, F or Cl;
provided that there may only be one each of CF₃, phenoxy or benzyloxy on each of the phenyl and indene rings;
X=(CH₂)n or —(CH₂)q—CH=CH(CH₂)q—;
n=1-3;
both q's=0, or one is 0 and the other is 1;
Z=—Q—CH₂—C(R₁₀)(OH)—CH₂COOH, in free acid form or in the form of an ester or delta-lactone or salt;
Q=CO, —C(OR₇)₂— or CHOH;
R'₇ₛ=the same primary or secondary 1-6C alkyl, or together are (CH₂)₂ or (CH₂)₃;
R₁₀=H or 1-3C alkyl;
provided that Q may be other than CHOH only when X is CH=CH or CH₂—CH=CH and/or R₁₀ is 1-3C alkyl.

Heathcock, J. Med. Chem., 1989, 32, 197 discloses the synthesis of a monocyclic compound of the structure

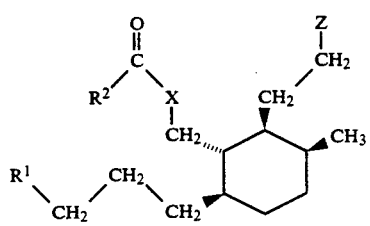

However, this compound is relatively inactive as an HG CoA reductase inhibitor.

DESCRIPTION OF THE INVENTION

In accordance with the present invention, compounds are provided having the structure and include all stereoisomers thereof, wherein Z is

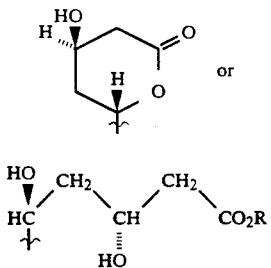

or

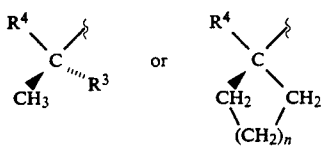

R is H, lower alkyl or metal ion such as an alkali metal, e.g. Na, Li or K.

$R^1$ is H, lower alkyl, aryl, lower alkoxy, cycloalkyl, heteroalkyl, aralkyl, heteroaralkyl or heterocyclic;

$R^2$ is lower alkyl, cycloalkyl or aralkyl, preferably

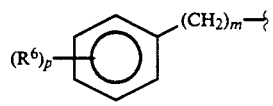

wherein $R^3$ is H or lower alkyl; n is 1, 2 or 3; and X is O or $NR^5$ wherein $R^5$ is H or lower alkyl, and $R^4$ is lower alkyl, lower thioalkyl, or

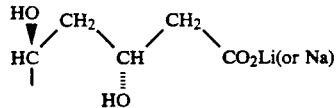

wherein m is 0, 1, 2 or 3, p is 0, 1 or 2 and $R^6$ is halogen, lower alkyl, hydroxy or lower alkoxy.

Thus, the compounds of the invention include the following types of compounds.

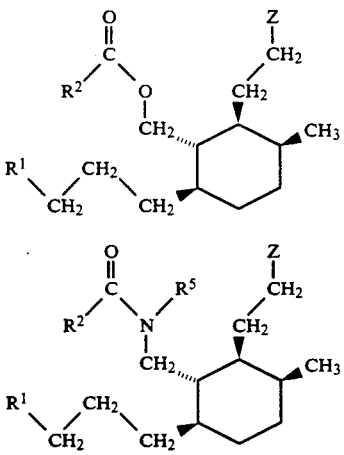

IA

IB

Preferred are compounds of structure I wherein $R^1$ is H, $R^2$ is

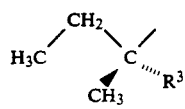

$R^3$ is $CH_3$, X is O or NH and Z

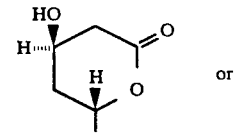

or

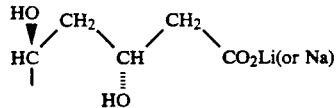

The term "lower alkyl" or "alkyl" as employed herein includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, alkoxy, aryl, alkylaryl, haloaryl, cycloalkyl, alkylcycloalkyl, hydroxy, alkoxycarbonyl, alkanoyloxy, aroyloxy, alkylthio, alkylsulfinyl, alkylsulfonyl, arylthio, arylsulfinyl and/or arylsulfonyl.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 of the following groups: halogen, lower alkoxy, lower alkyl, hydroxy, lower alkoxycarbonyl, lower alkanoyl, aroyl, aryl, alkylthio, alkylsulfinyl, alkylsulfonyl, cycloalkylthio, cycloalkylsulfinyl, cycloalkylsulfonyl, arylthio and/or oxo.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 of the following groups, lower alkyl, halogen (Cl, Br, F or $CF_3$), lower alkoxy, nitro, alkoxy and/or cyano.

The term "aralkyl", "aryl-alkyl" or "aryl-lower alkyl" as used herein refers to lower alkyl groups as discussed above having an aryl substituent, such as benzyl.

The term "lower alkoxy", "alkoxy" or "aralkoxy" includes any of the above lower alkyl, alkyl or aralkyl groups linked to an oxygen atom.

The term "halogen" or "halo" as used herein refers to chlorine, bromine, fluorine or iodine, with chlorine being preferred.

The term "lower alkenyl" as used herein refers to straight or branched chain radicals of 2 to 12 carbons, preferably 2 to 6 carbons in the normal chain, which include one double bond in the normal chain, such as 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl and the like.

The terms "alkanoyl" and "aroyl" refer to a lower alkyl group linked to a carbonyl group or an aryl group linked to a carbonyl group.

The term "haloalkyl" as used herein refers to any of the lower alkyl groups defined above substituted with a halogen as defined above, for example $CH_2F$, $CF_3$ and the like.

The term "metal ion" refers to alkali metal ions such as sodium, potassium or lithium and alkaline earth metal ions such as magnesium and calcium.

The term "heteroaryl" as used herein refers to a 5 to 10 membered mono or bicyclic ring which includes one or two hetero atoms, namely, N, S or O, such as 3-pyrrolyl, 2-imidazolyl, 2-thiazolyl, 2-oxazolyl, 3-pyridyl, 2-pyridyl, 3-aminopyridinyl, pyrazinyl, 2-pyrimidinyl, 2-indolizinyl, 2-thienyl, 3-furyl, 2-quinolyl, 1-indolyl, 5-isothiazolyl, 5-isoxazoyl, and the like.

The term heteroaralkyl as used herein refers to any of the above hetero groups linked to an alkylene group.

The term "heterocyclic" or "hetero" as used herein alone or a part of another group refers to 5- to 10-membered, preferably 5 to 8 membered, monocyclic or bicyclic heterocyclic rings containing 1 or 2 hetero atoms such as N; N and O; and N and S and includes piperidino, pyrrolidino, morpholino, thiamorpholino, piperazino, homopiperazino, piperidinyl, pyrrolidinyl, piperazinyl, morpholinyl, thiamorpholinyl, histaminyl, and the like.

The compounds of the invention may be prepared as described below.

The method for preparing the compounds of formula I wherein X is O, that is compounds of formula IA, is set out in the following Reaction Scheme I.

The method for preparing compounds of formula I where X is NR$^5$, that is compounds of formula IB, is set out in the following Reaction Scheme II.

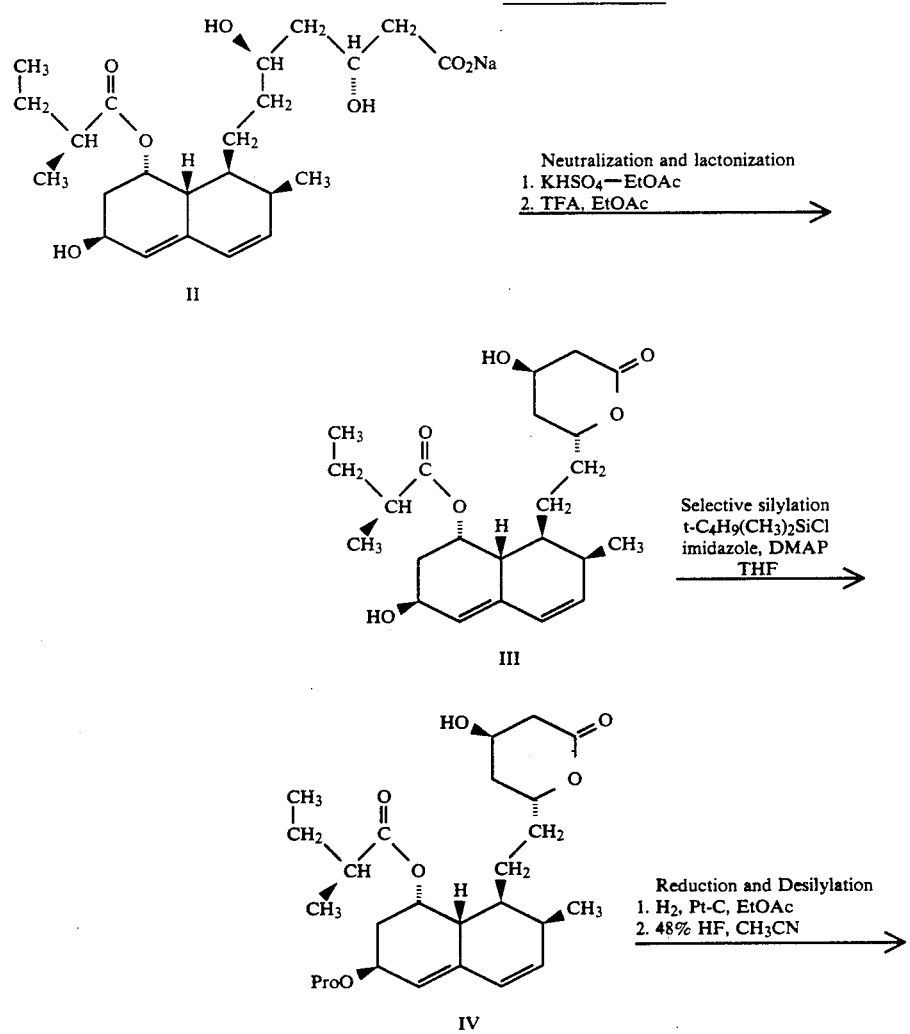

-continued
Reaction Scheme I
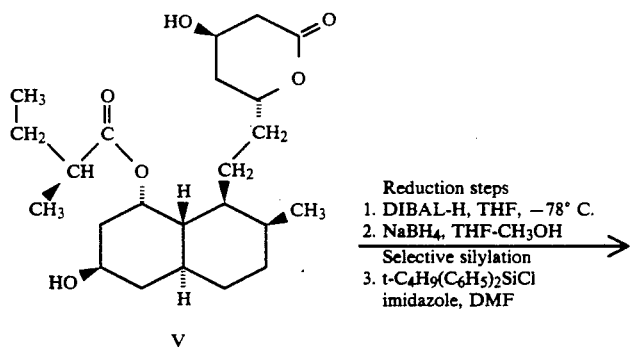
V
Reduction steps
1. DIBAL-H, THF, −78° C.
2. NaBH₄, THF-CH₃OH
Selective silylation
3. t-C₄H₉(C₆H₅)₂SiCl
   imidazole, DMF
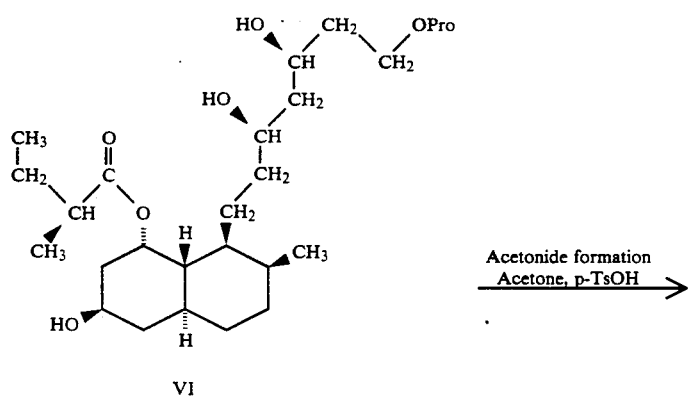
VI
Acetonide formation
Acetone, p-TsOH
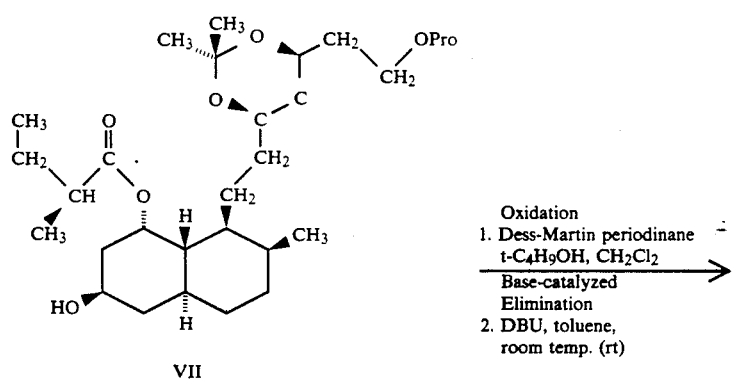
VII
Oxidation
1. Dess-Martin periodinane
   t-C₄H₉OH, CH₂Cl₂
Base-catalyzed Elimination
2. DBU, toluene,
   room temp. (rt)
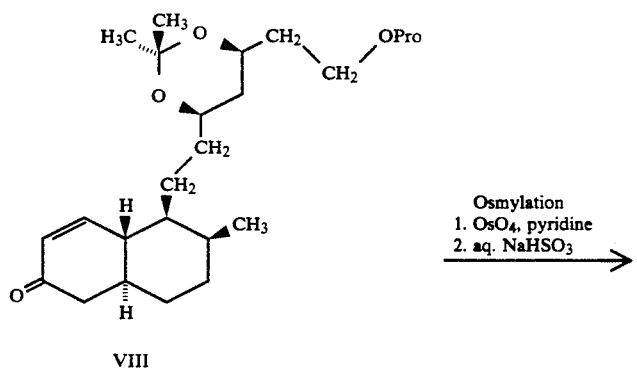
VIII
Osmylation
1. OsO₄, pyridine
2. aq. NaHSO₃

-continued
Reaction Scheme I
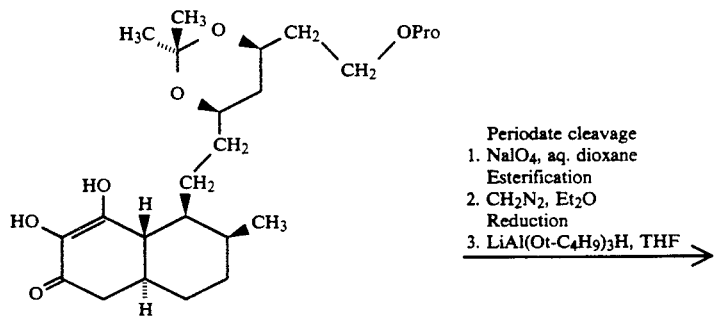
IX
Periodate cleavage
1. NaIO₄, aq. dioxane
Esterification
2. CH₂N₂, Et₂O
Reduction
3. LiAl(Ot-C₄H₉)₃H, THF
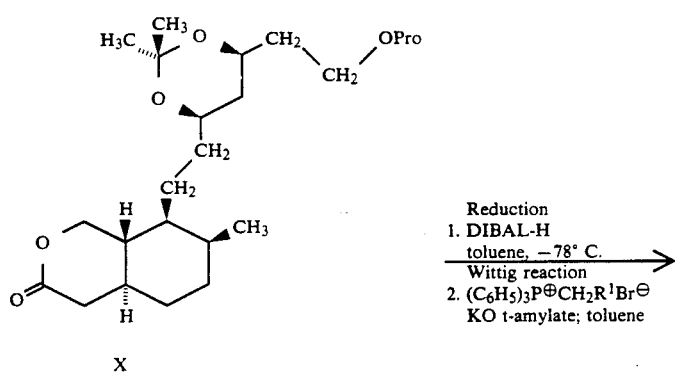
X
Reduction
1. DIBAL-H
toluene, −78° C.
Wittig reaction
2. (C₆H₅)₃P⊕CH₂R¹Br⊖
KO t-amylate; toluene
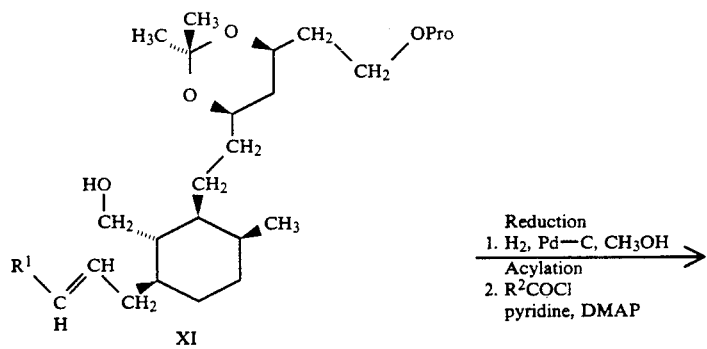
XI
Reduction
1. H₂, Pd—C, CH₃OH
Acylation
2. R²COCl
pyridine, DMAP
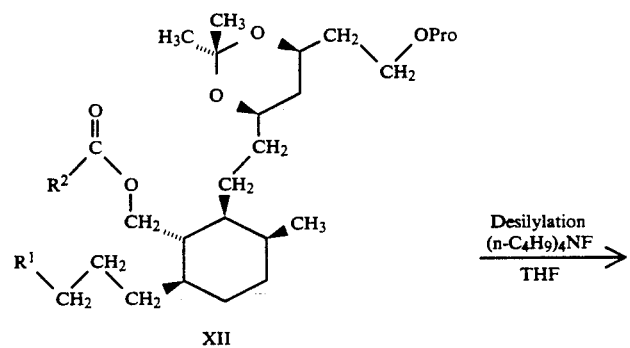
XII
Desilylation
(n-C₄H₉)₄NF
THF

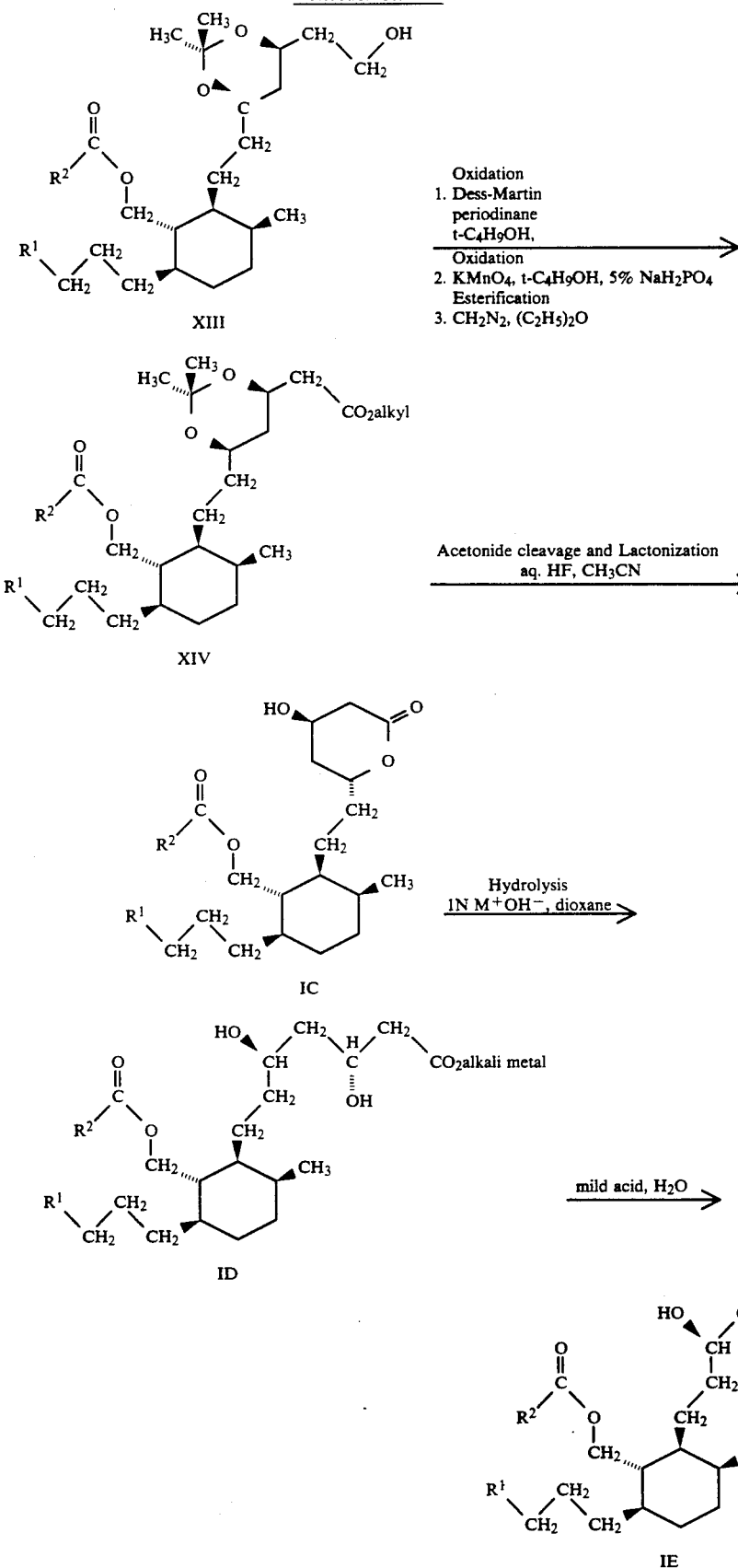

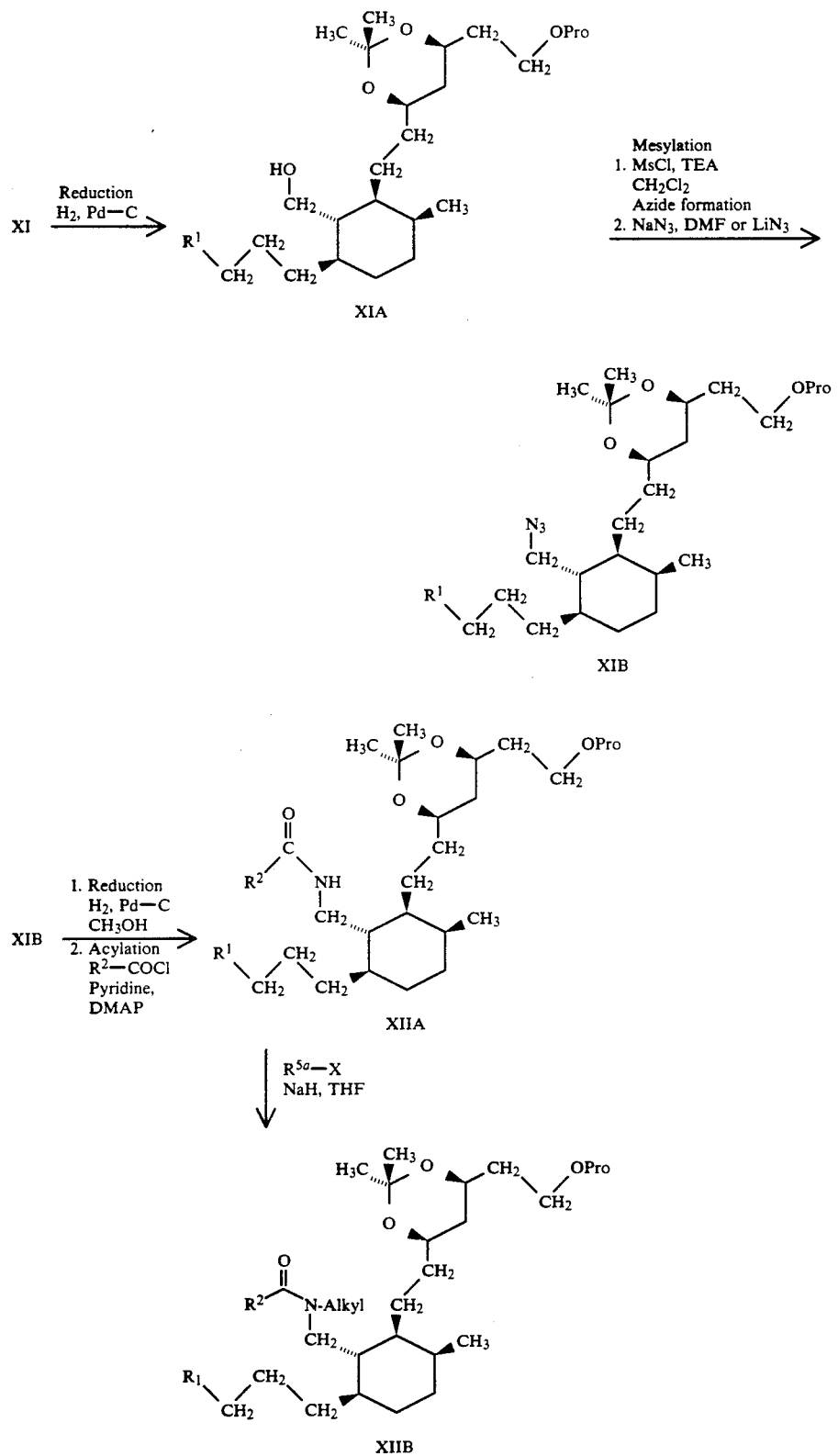
XIIA or XIIB employed in place of XII in Reaction Scheme I to form the following compounds:

-continued
Reaction Scheme II
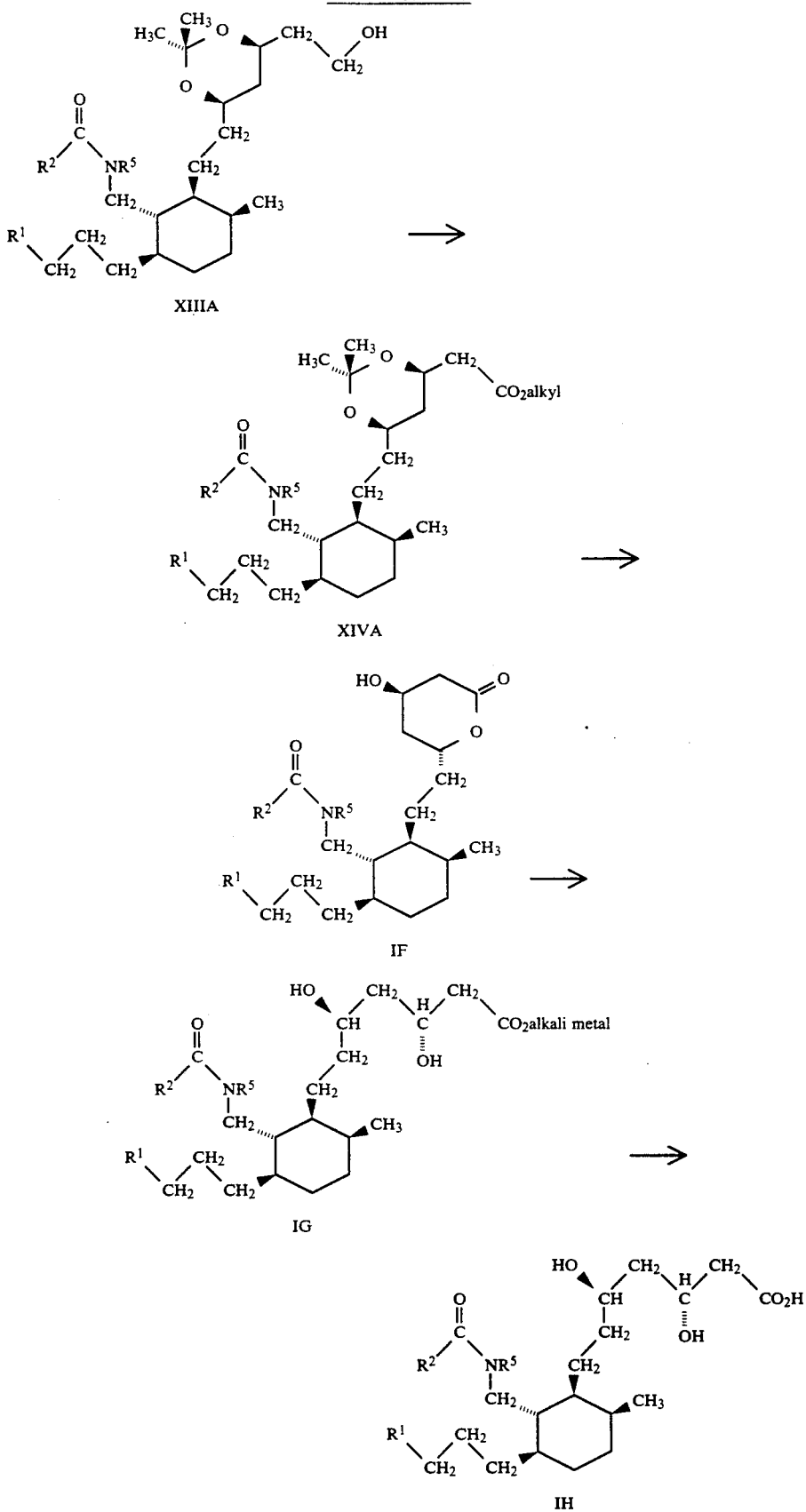

Referring to the Reaction Scheme I set out hereinbefore, compounds of formula IA (X is O) are prepared starting with pravastatin (compound II) which is converted to the corresponding free acid by treating II with mild aqueous acid such as potassium bisulfate, hydrochloride acid or sulfuric acid in the presence of a solvent such as ethyl acetate (EtOAc) or dichloromethane. The resulting free acid is subjected to lactonization by treating a solution of same in an inert organic solvent such as ethyl acetate or dichloromethane with trifluoroacetic (TFA) or hydrofluoric acid employing a molar ratio of acid:free acid of within the range of from about 0.1:1 to about 0.2:1, for a period of from about 16 to about 24 hours.

Lactone III is dissolved in, for example, methylene chloride or tetrahydrofuran, and then treated with amine base such as imidazole, triethylamine, ethyldiisopropylamine or N,N-dimethylaniline and then with a silyl chloride protecting agent (ProCl) such as tertiary-butyldimethylsilyl chloride, tertiary-butyldiphenylsilyl chloride, triethylsilyl chloride or phenyldimethylsilyl chloride, and an appropriate catalyst such as 4-(N,N-dimethylamino)pyridine (DMAP), for a period of from about 8 to about 24 hours, preferably from about 12 to about 16 hours, to form the protected compound IV. In carrying out the above reaction the amine base is employed in a molar ratio to the lactone III of within the range of from about 1:1 to about 1.2:1 and the silyl chloride protecting agent is employed in a molar ratio to lactone III of within the range of from about 1:1 to about 1.1:1.

The protected compound IV is then hydrogenated by treatment with hydrogen (for a period of from about 4 to about 24 hours) in the presence of a hydrogenation catalyst such as platinum on carbon, palladium on carbon or platinum oxide, and the crude reduction product is desilylated by treatment with hydrofluoric acid (for a period of from about 0.5 to about 1.5 hours) in the presence of an organic solvent such as acetonitrile under an inert atmosphere such as argon, employing a molar ratio of crude reaction product:HF of within the range of from about 1:2 to about 1:5, to form the compound V.

Compound V is then reduced by treating a solution of V in an inert organic solvent such as tetrahydrofuran, dichloromethane or toluene, with diisobutylaluminum hydride (DIBAL-H), under an inert atmosphere such as argon, at a temperature within the range of from about $-80°$ C. to about $-40°$ C., for a period of from about 0.5 to about 2 hours, to form a crude lactol which is suspended under an inert atmosphere such as argon in an inert organic solvent such as tetrahydrofuran, and treated with sodium borohydride and an alcohol solvent such as methanol or ethanol, at a temperature within the range of from about $0°$ C. to about $25°$ C., to form crude tetraol. The crude tetraol, with further purification, is dissolved in dry inert organic solvent such as dry dimethylformamide (DMF), under an inert atmosphere such as argon, and selectively silylated by treating with a base such as imidazole and the like as described above, silylating agent (ProCl), as described above, using the procedure as described hereinbefore, to form the silylated compound VI. Compound VI is then converted to the corresponding acetonide by treating with p-toluenesulfonic acid monohydrate (p-TsOH) in the presence of dry acetone for a period of from about 4 to about 16 hours, to form the acetonide compound VII.

Compound VII is then oxidized via a Dess-Martin periodinane by admixing a solution of Dess-Martin periodinane in an inert organic solvent such as methylene chloride, under an inert atmosphere such as argon, with t-butanol and a solution of VII in an inert organic solvent such as methylene chloride for a period of from about 0.5 to about 2 hours, employing a molar ratio of periodinane:VII of within the range of from about 1:1 to about 1.5:1. The crude product is purified and made to undergo base-catalyzed elimination by forming a solution of the purified product with an aromatic solvent such as toluene or benzene and treating the solution with diazobicycloundecane (DBU), for a period of from about 1 to about 2 hours, to form compound VIII. Compound VIII is dissolved in dry pyridine and is treated with a solution of $OsO_4$ in dry pyridine under an inert atmosphere such as argon, employing a molar ratio of $OsO_4$:VIII of within the range of from about 1:1 to about 1.1:1, for a period of from about 1 to about 4 hours, to form IX.

To a solution of compound IX in dioxane, under an inert atmosphere such as argon, is added a solution of sodium periodate in water (employing a molar ratio of IX:periodate of from about 1:2 to about 1:2.5), the resulting reaction is allowed to proceed for a period of from about 12 to about 18 hours. The resulting crude product is taken up in a solvent such as diethyl ether, cooled and treated with etherial diazomethane to form an aldehyde which is dissolved in dry tetrahydrofuran, at a temperature of from about $-10°$ to about $0°$ C., and treated under an inert atmosphere such as argon, with a reducing agent such as $LiAl(Ot-C_4H_9)_3H$, to form compound X.

Compound X is then reduced by treating a solution of X in dry organic solvent such as toluene, dichloromethane or tetrahydrofuran, with diisobutylaluminum hydride (DIBAL-H), in dry organic solvent such as toluene, under an inert atmosphere such as argon, at a temperature of from about $-80°$ to about $-40°$ C., for a period of from about 0.5 to about 2 hours, to form crude lactol which is subjected to a Wittig reaction as follows. A suspension of a triphenylphosphonium bromide of the structure A

 (A)

in dry organic solvent such as toluene, or tetrahydrofuran, at a temperature of from about $-20°$ to about $0°$ C., under an inert atmosphere such as argon, is treated with a solution of potassium t-amylate or potassium bis(trimethylsilyl)amide in dry organic solvent such as toluene, or tetrahydrofuran. After stirring the mixture for about 0.5 to about 2 hours, a solution of the above crude lactol in dry organic solvent such as toluene or tetrahydrofuran is reacted with the mixture, at a temperature of from about $0°$ to about $25°$ C., for a period of from about 1 to about 3 hours, employing a molar ratio of lactol:phosphonium compound A of within the range of from about 1:2 to about 1:4, to form alcohol XI. Alcohol XI is reduced by treating with hydrogen (for a period of from about 1 to about 2 hours) in the presence of a hydrogenation catalyst such as palladium on carbon, platinum on carbon or platinum oxide, and an alcohol solvent such as methanol or ethanol. The crude product is then acylated by treating same with an acylating agent of the structure B $R^2COCl$ B employing a molar ratio of reduced alcohol:B of within the range of from about 1:1 to about 1:2 in the presence of base such as pyridine and 4-(N,N-dimethylamino)-pyridine (DMAP), under an inert atmosphere such as argon, at a temperature of from about 0° to about 25° C., for a period of from about 8 to about 24 hours, to form ester XII.

Ester XII is made to undergo desilylation by treating a solution of XII in dry organic solvent such as tetrahydrofuran, under an inert atmosphere such as argon, with a desilylating agent such as (n—$C_4H_9$)$_4$NF, in an organic solvent such as tetrahydrofuran, for a period of from about 8 to about 24 hours, employing a molar ratio of XII: disilylating agent of from about 1:1 to about 1:3, to form alcohol XIII.

Compound XIII is then oxidized via Dess-Martin periodinane by admixing a solution of Dess-Martin periodinane in an inert organic solvent such as methylene chloride, under an inert atmosphere such as argon, with t-butanol and a solution of XIII in an inert organic solvent such as methylene chloride, for a period of from about 0.5 to about 2 hours, employing a molar ratio of periodinane:XIII of within the range of from about 1:1 to about 1.5:1. The crude aldehyde is taken up in an organic solvent such as t-butanol and 5% aqueous $NaH_2PO_4$, and treated with oxidizing agent such as potassium permanganate, for a period of from about 5 to about 15 minutes, employing a molar ratio of crude aldehyde:oxidizing agent of from about 1:5 to about 1:10, to form crude acid which is esterified by treatment with etherial diazoalkane such as diazomethane, diazoethane, or phenyldiazomethane, to form the ester XIV.

Ester XIV is subjected to acetonide cleavage and lactonization by treating a solution of XIV, in a mixture of aqueous hydrofluoric acid and acetonitrile for a period of from about 4 to about 8 hours, to form the lactone of the invention IC.

The formula IC compound of the invention may be hydrolyzed by treating IC with aqueous alkali metal base to form the compound ID of the invention.

Referring to the Reaction Scheme II set out hereinbefore, compounds of formula IB (X is $NR^5$) are prepared starting with alcohol XI which is reduced by treatment with hydrogen in the presence of a catalyst such as palladium on charcoal and an alcohol solvent such as methanol, to form XIA. XIA is mesylated by reacting XIA with methanesulfonyl chloride in the presence of triethylamine or other base such as diisopropylethylamine, in the presence of an inert organic solvent such as methylene chloride to form crude mesylate, followed by displacement with lithium or sodium azide by treating the mesylate with lithium or sodium azide in the presence of dimethylformamide at a temperature of from about 25° to about 75° C., for a period of from about 2 to about 8 hours, to form the azide compound XIB.

Azide XIB is then reduced by treatment with hydrogen in the presence of palladium on charcoal and alcohol solvent such as methanol or ethanol and the resulting compound is acylated by treatment with acylating agent B

$R^2COCl$  B employing a molar ratio of amine:B of within the range of from about 1:1 to about 1:3, in the presence of base such as pyridine and 4-(N,N-dimethylamino)pyridine (DMAP), under an inert atmosphere such as argon, at a temperature of from about 0° to about 25° C., for a period of from about 0.5 to about 2 hours, to form amide XIIA.

Amide XIIA may be used in place of ester XII in Reaction Scheme I to form compounds XIIIA, XIVA, IF and IG where $R^5$ is H.

Compounds of the invention of formula I where X is $NR^5$, and $R^5$ is alkyl may be prepared by treating amide XIIA with a base such as sodium hydride, or potassium t-butoxide and an alkylhalide $R^{5a}$-X (where $R^{5a}$ is alkyl and X is bromine or iodine) in a solvent such as tetrahydrofuran or dimethylfuramide, at a temperture of from about 25° to about 50° C., for a period of from about 2 to about 16 hours, employing a molar ratio of base:XIIA of from about 1:1 to about 1.1:1 and a molar ratio of alkyl halide:XIIA of from about 1:1 to about 3:1, to form amide XIIB.

Amide XIIB may be used in place of amide XII in Reaction Scheme I to form compounds XIIIA, XIVA, IF AND IG, where $R^5$ is alkyl.

Compounds of the invention where R is lower alkyl may be prepared as follows.

Esters, preferably alkyl esters, of the carboxylic acids of formula IE or IH may be obtained by contacting the carboxylic acid of formula IE or IH with an appropriate alcohol, preferably in the presence of an acid catalyst, for example a mineral acid (such as hydrochloric acid or sulphuric acid), a Lewis acid (for example boron trifluoride) or an ion exchange resin. The solvent employed for this reaction is not critical, provided that it does not adversely affect the reaction: suitable solvents include benzene, chloroform, ethers and the like. Alternatively, the desired product may be obtained by contacting the carboxylic acid of formula IE or IH with a diazoalkane, in which the alkane moiety may be substituted or unsubstituted. This reaction is usually effected by contacting the acid with an ethereal solution of the diazoalkane. As a further alternative, the ester may be obtained by contacting a metal salt of the carboxylic acid of formula IE or IH with a halide, preferably an alkyl halide, in a suitable solvent: preferred solvents include dimethylformamide, tetrahydrofuran, dimethylsulfoxide and acetone. All of the reactions for producing esters are preferably effected at about ambient temperature, but, if required by the nature of the reaction system, the reactions may be conducted with heating.

Compound IE or IH of the invention is obtained by Careful acidification of an aqueous solution of compound ID or IG with an acid such as aqueous potassium bisulfate followed by extraction of IE or IH from the aqueous mixture with an organic solvent such as ethyl acetate, dichloromethane or chloroform. The organic extracts are then dried with $MgSO_4$ or $Na_2SO_4$, filtered and concentrated to provide IE or IH.

Compounds of the invention of formula I where R is lower alkyl may also be obtained by adding to a solution of compound IC or IF in an appropriate alcohol a slight molar excess of the corresponding alkoxide. The mixture is then diluted with an organic solvent such as ethyl acetate or chloroform and extracted with water. The organic portion is dried with $MgSO_4$ or $Na_2SO_4$, filtered and concentrated to provide lower alkyl ester of compounds of formula 1.

Alternatively, compounds of the invention of formula I where R is lower alkyl are obtained by solvolysis of the lactone IC or IF in the presence of an appropriate alcohol and an acid catalyst, which may be an inorganic acid such as hydrochloric acid or sulphuric acid, a Lewis acid such as boron trifluoride or an acidic ion-exchange resin. In the case of an inorganic acid or Lewis acid, isolation of the product ester involves neutralization and extraction followed by drying, filtering and concentrating. In the case of an ion exchange resin, simple filtration and concentration will provide the product ester.

The compounds of formula I of the invention will be formulated with a pharmaceutical vehicle or diluent. The pharmaceutical composition can be formulated in a classical manner utilizing solid or liquid vehicles or diluents and pharmaceutical additives of a type appropriate to the mode of desired administration. The compounds can be administered by an oral route, for example, in the form of tablets, capsules, granules or powders, or they can be administered by a parenteral route in the form of injectable preparations.

A typical capsule for oral administration contains active ingredients (25 mg), lactose (75 mg) and magnesium stearate (15 mg). The mixture is passed through a 60 mesh sieve and packed into a No. 1 gelatin capsule.

A typical injectable preparation is produced by asceptically placing 25 mg of a water soluble salt of sterile active ingredient into a vial, asceptically freeze-drying and sealing. For use, the contents of the vial are mixed with 2 ml of physiological saline, to produce an injectable preparation.

New intermediates in accordance with the present invention may be represented by the following formulae:

A.

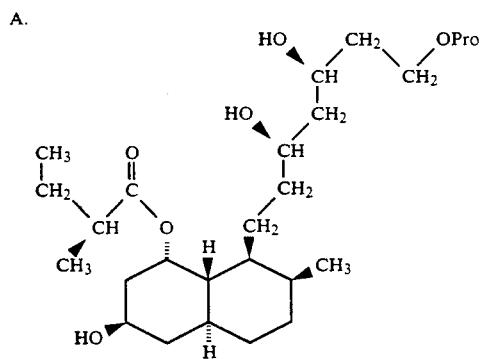

B.

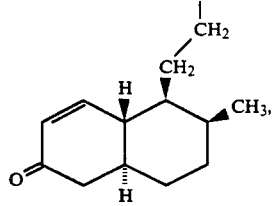

where Q is

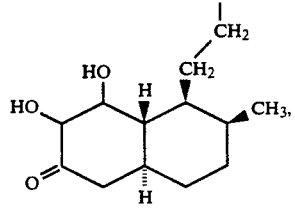

VIII

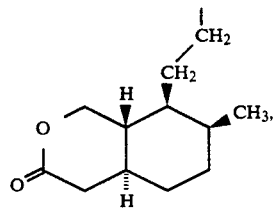

IX

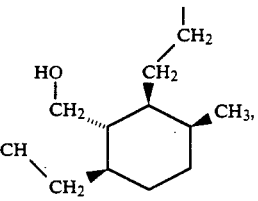

X

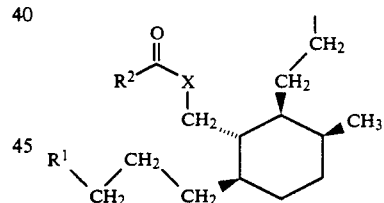

XI

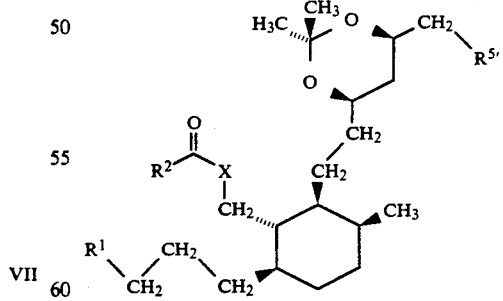

XII, XIIA, XIIB

XIII, XIIIA, XIV, XIVA where $R^{5'}$ $CH_2OH$ or $CO_2alkyl$.

The compounds of the invention are inhibitors of 3-hydroxy-3-methylglutaryl coenzyme A (HMG-CoA) reductase and inhibit cholesterol biosynthesis. Such compounds are useful in treating atherosclerosis to inhibit progression of disease, in treating hyperlipidemia to inhibit development of atherosclerosis, and in treating nephrotic hyperlipidemia. In addition, the compounds of the invention increase plasma high density lipoprotein cholesterol levels and lower plasma low density and intermediate density lipoprotein cholesterol levels.

As HMG CoA reductase inhibitors, the compounds of the invention may also be useful in inhibiting formation of gallstones and in treating tumors.

The compounds of the invention may also be employed in combination with an antihyperlipoproteinemic agent such as probucol and/or with one or more serum cholesterol lowering agents such as Lopid (gemfibrozil), bile acid sequestrants such as cholestyramine, colestipol, DEAE-Sephadex as well as clofibrate, nicotinic acid and its derivatives, neomycin, p-aminosalicyclic acid, lovastatin, pravastatin, visinolin (velostatin, symvastatin or sinvinolin) and the like, and/or one or more squalene synthetase inhibitors.

The above compounds to be employed in combination with the HMG CoA reductase inhibitor of the invention will be used in amounts as indicated in the Physicians' Desk Reference (PDR).

The compounds of this invention also have useful antifungal activities. For example, they may be used to control strains of Penicillium sp., Aspergillus niger, Cladosporium sp., Cochliobolus miyabeorus and Helminthosporium cynodnotis. For those utilities they are admixed with suitable formulating agents, powders, emulsifying agents or solvents such as aqueous ethanol and sprayed or dusted on the plants to be protected.

In addition, the compounds of the invention may be useful in elevating HDL-cholesterol while lowering levels of LDL-cholesterol and serum triglycerides, and for treating tumors.

The compounds of the invention prepared as described above are single, homochiral diastereomers. The compounds of the described absolute stereochemistry are preferred, but compounds with the opposite stereochemistry at one or more of the stereocenters are also within the scope of the present invention.

The compounds of the invention are inhibitors of 3-hydroxy-3-methyl-glutaryl coenzyme A (HMG-CoA) reductase and thus are useful in inhibiting cholesterol biosynthesis as demonstrated by the following tests.

1) Rat Hepatic HMG-CoA Reductase

Rat hepatic HMG-CoA reductase activity is measured using a modification of the method described by Edwards (Edwards, P. A., et al., J. Lipid Res. 20:40, 1979). Rat hepatic microsomes are used as a source of enzyme, and the enzyme activity is determined by measuring the conversion of the $^{14}$C-HMG-CoA substrate to $^{14}$C-mevalonic acid.

a. Preparation of Microsomes

Livers are removed from 2-4 cholestyramine-fed, decapitated, Sprague Dawley rats, and homogenized in phosphate buffer A (potassium phosphate, 0.04M, pH 7.2; KCl, 0.05M; sucrose, 0.1M; EDTA, 0.03M; aprotinin, 500 KI units/ml). The homogenate is spun at 16,000×g for 15 minutes at 4° C. The supernatant is removed and recentrifuged under the same conditions a second time. The second 16,000×g supernatant is spun at 100,000×g for 70 minutes at 4° C. Pelleted microsomes are resuspended in a minimum volume of buffer A (3-5 ml per liver), and homogenized in a glass/glass homogenizer. Dithiothreitol is added (10 mM), and the preparation is aliquoted, quick frozen in acetone/dry ice, and stored at −80° C. The specific activity of the first microsomal preparation was 0.68 nmole mevalonic acid/mg protein/minute.

b. Enzyme Assay

The reductase is assayed in 0.25 ml which contains the following components at the indicated final concentrations:

| | | |
|---|---|---|
| 0.04 | M | Potassium phosphate, pH 7.0 |
| 0.05 | M | KCl |
| 0.10 | M | Sucrose |
| 0.03 | M | EDTA |
| 0.01 | M | Dithiothreitol |
| 3.5 | mM | NaCl |
| 1% | | Dimethylsulfoxide |
| 50–200 | µg | Microsomal protein |
| 100 | µM | $^{14}$C-[DL]HMG-CoA (0.05 µCi, 30–60 mCi/mmole) |
| 2.7 | mM | NADPH (nicotinamide adenine dinucleotide phosphate) |

Reaction mixtures are incubated at 37° C. Under conditions described, enzyme activity increases linearly up to 300 µg microsomal protein per reaction mixture, and is linear with respect to incubation time up to 30 minutes. The standard incubation time chosen for drug studies is 20 minutes, which results in 12-15% conversion of HMG-CoA substrate to the mevalonic acid product. [DL-]HMG-CoA substrate is used at 100 µM, twice the concentration needed to saturate the enzyme under the conditions described. NADPH is used in excess at a level 2.7 times the concentration required to achieve maximum enzyme velocity.

Standardized assays for the evaluation of inhibitors are conducted according to the following procedure. Microsomal enzyme is incubated in the presence of NADPH at 37° C. for 15 minutes. DMSO vehicle with or without test compound is added, and the mixture further incubated for 15 minutes at 37° C. The enzyme assay is initiated by adding $^{14}$C-HMG-CoA substrate. After 20 minutes incubation at 37° C. the reaction is stopped by the addition of 25 µl of 33% KOH. $^3$H-mevalonic acid (0.05 µCi) is added, and the reaction mixture allowed to stand at room temperature for 30 minutes. Fifty µl 5N HCl is added to lactonize the mevalonic acid. Bromophenol blue is added as a pH indicator to monitor an adequate drop in pH. Lactonization is allowed to proceed for 30 minutes at room temperature. Reaction mixtures are centrifuged for 15 minutes at 2800 rpm. The supernatants are layered onto 2 grams AG 1-X8 anion exchange resin (Biorad, formate form) poured in 0.7 cm (id) glass columns, and eluted with 2.0 ml H$_2$O. The first 0.5 ml is discarded, and the next 1.5 ml is collected and counted for both tritium and carbon 14 in 10.0 ml Opti-fluor scintillation fluid. Results are calculated as nmoles mevalonic acid produced per 20 minutes, and are corrected to 100% recovery of tritium. Drug effects are expressed as $I_{50}$ values (concentration of drug producing 50% inhibition of enzyme activity) derived from composite dose response data with the 95% confidence interval indicated.

Conversion of drugs in lactone form to their sodium salts is accomplished by solubilizing the lactone in DMSO, adding a 10-fold molar excess of NaOH, and allowing the mixture to stand at room temperature for 15 minutes. The mixture is then partially neutralized (pH 7.5-8.0) using 1N HCl, and diluted into the enzyme reaction mixture.

2) Cholesterol Synthesis in Freshly Isolated Rat Hepatocytes

Compounds which demonstrate activity as inhibitors of HMG-CoA reductase are evaluated for their ability to inhibit $^{14}$C-acetate incorporation into cholesterol in freshly isolated rat hepatocyte suspensions using methods originally described by Capuzzi et al. (Capuzzi, D. M. and Margolis, S., Lipids, 6:602, 1971).

a. Isolation of Rat Hepatocytes

Sprague Dawley rats (180-220 grams) are anesthetized with Nembutol (50 mg/kg). The abdomen is opened and the first branch of the portal vein is tied closed. Heparin (100-200 units) is injected directly into the abdominal vena cava. A single closing suture is placed on the distal section of the portal vein, and the portal vein is canulated between the suture and the first branching vein. The liver is perfused at a rate of 20 ml/minute with prewarmed (37° C.), oxygenated buffer A (HBSS without calcium or magnesium containing 0.5 mM EDTA) after severing the vena cava to allow drainage of the effluent. The liver is additionally perfused with 200 ml of prewarmed buffer B (HBSS containing 0.05% bacterial collagenase). Following perfusion with buffer B, the liver is excised and decapsulated in 60 ml Waymouth's medium allowing free cells to disperse into the medium. Hepatocytes are isolated by low speed centrifugation for 3 minutes at 50×g at room temperature. Pelleted hepatocytes are washed once in Waymouth's medium, counted and assayed for viability by trypan blue exclusion. These hepatocyte enriched cell suspensions routinely show 70-90% viability.

b. $^{14}$C-Acetate Incorporation into Cholesterol

Hepatocytes are resuspended at $5 \times 10^6$ cells per 2.0 ml in incubation medium (IM) [0.02M Tris-HCl (pH 7.4), 0.1M KCl, 0.33 $MgCl_2$, 0.22 mM sodium citrate, 6.7 mM nicotinamide, 0.23 mM NADP, 1.7 mM glucose-6-phosphate].

Test compounds are routinely dissolved in DMSO or DMSO:$H_2O$ (1:3) and added to the IM. Final DMSO concentration in the IM is $\leq 1.0\%$, and has no significant effect on cholesterol synthesis.

Incubation is initiated by adding $^{14}$C-acetate (58 mCi/mmol, 2 $\mu$Ci/ml), and placing the cell suspensions (2.0 ml) in 35 mm tissue culture dishes, at 37° C. for 2.0 hours. Following incubation, cell suspensions are transferred to glass centrifuge tubes and spun at 50×g for 3 minutes at room temperature. Cell pellets are resuspended and lysed in 1.0 ml $H_2O$, and placed in an ice bath.

Lipids are extracted essentially as described by Bligh, E. G. and W. J. Dyer, Can. J. Biochem. and Physiol., 37:911, 1959. The lower organic phase is removed and dried under a stream of nitrogen, and the residue resuspended in (100 $\mu$l) chloroform:methanol (2:1). The total sample is spotted on silica gel (LK6D) thin-layer plates and developed in hexane:ethyl ether:acetic acid (75:25:1). Plates are scanned and counted using a BioScan automated scanning system. Radiolabel in the cholesterol peak (RF 0.28) is determined and expressed at total counts per peak and as a percent of the label in the total lipid extract. Cholesterol peaks in control cultures routinely contain 800-1000 cpm, and are 9-20% of the label present in the total lipid extract; results compatable with Capuzzi, et al., indicating 9% of extracted label in cholesterol.

Drug effects (% inhibition of cholesterol synthesis) are determined by comparing % of label in cholesterol for control and drug treated cultures. Dose response curves are constructed from composite data from two or more studies, and results are expressed as $I_{50}$ values with a 95% confidence interval.

3) Cholesterol Synthesis in Human Skin Fibroblasts

Compound selectivity favoring greater inhibitory activity in hepatic tissue would be an attribute for a cholesterol synthesis inhibitor.

Therefore, in addition to evaluating cholesterol synthesis inhibitors in hepatocytes, these compounds are also tested for their activity as inhibitors of cholesterol synthesis in cultured fibroblasts.

a. Human Skin Fibroblast Cultures

Human skin fibroblasts (passage 7-27) are grown in Eagles' minimal essential medium (EM) containing 10% fetal calf serum. For each experiment, stock cultures are trypsonized to disperse the cell monolayer, counted, and plated in 35 mm tissue culture wells ($5 \times 10^5$ cells/2.0 ml). Cultures are incubated for 18 hours at 37° C. in 5% $CO_2$/95% humidified room air. Cholesterol biosynthetic enzymes are induced by removing the serum containing medium, washing the cell monolayers, and adding 1.0 ml of EM containing 1.0% fatty acid free bovine serum albumin, and incubating the cultures an additional 24 hours.

b. $^{14}$C-Acetate Incorporation into Cholesterol

Induced fibroblast cultures are washed with $EMEM_{100}$ (Earle's minimal essential medium). Test compounds are dissolved in DMSO or DMSO:EM (1:3) (final DMSO concentration in cell cultures $\leq 1.0\%$), added to the cultures, and the cultures preincubated for 30 minutes at 37° C. in 5% $CO_2$/95% humidified room air. Following preincubation with drugs, [1-$^{14}$C]Na acetate (2.0 $\mu$Ci/ml, 58 mCi/mmole) is added, and the cultures reincubated for 4 hours. After incubation, the culture medium is removed, and the cell monolayer (200 $\mu$g cell protein per culture) is scraped into 1.0 ml of $H_2O$. Lipids in the lysed cell suspension are extracted into chloroform:methanol as described for hepatocyte suspensions. The organic phase is dried under nitrogen, and the residue resuspended in chloroform:methanol (2:1) (100 $\mu$l), and the total sample spotted on silica gel (LK6D) thin-layer plates, and analyzed as described for hepatocytes.

Inhibition of cholesterol synthesis is determined by comparing the percent of label in the cholesterol peak from control and drug-treated cultures. Results are expressed as $I_{50}$ values, and are derived from composite dose response curves from two or more experiments. A 95% confidence interval for the $I_{50}$ value is also calculated from the composite dose response curves.

A further aspect of the present invention is a pharmaceutical composition consisting of at least one of the compounds of formula I in association with a pharmaceutical vehicle or diluent. The pharmaceutical composition can be formulated employing conventional solid or liquid vehicles of diluents and pharmaceutical additives of a type appropriate to the mode of desired administration. The compounds can be administered by an oral route, for example, in the form of tablets, capsules, granules or powders, or they can be administered by a parenteral route in the form of injectable preparations, such dosage forms containing from 1 to 2000 mg of active compound per dosage, for use in the treatment. The dose to be administered depends on the unitary dose, the symptoms, and the age and the body weight of the patient.

The compounds of formula I may be administered in a similar manner and in amounts as known compounds suggested for use in inhibiting cholesterol biosynthesis, such as lovastatin or pravastatin, in mammalian species such as humans, dogs, cats and the like. Thus, the compounds of the invention may be administered in an amount from about 4 to 2000 mg in a single dose or in the form of individual doses from 1 to 4 times per day, preferably 4 to 200 mg in divided dosages of 1 to 100 mg, suitably 0.5 to 50 mg 2 to 4 times daily or in sustained release form.

The following working examples represent preferred embodiments of the invention. Unless otherwise specified, all temperature are in degrees Centigrade (°C.).

EXAMPLE 1

[1S-[1α,2β(2S*,4S*),3β,6β]]-2,2-Dimethylbutanoic acid,
[3-methyl-6-propyl-2-[2-(tetrahydro-4-hydroxy-6-oxo-2H-pyran-2-yl)ethyl]cyclohexyl]methyl ester

A.
[1S-[1α(R*),3β,7β,8β(2S*,4S*),8aβ]]-2-Methylbutanoic acid,
1,2,3,7,8,8a-hexa-hydro-3-hydroxy-7-methyl-8-[2-(tetrahydro-4-hydroxy-6-oxo-2H-pyran-2-yl)ethyl]-1-naphthalenyl ester Pravastatin (sodium salt) (10.05 g, 22.5 mmol) was converted to the corresponding free acid by partitioning between ethyl acetate (75 mL) and 5% KHSO$_4$ (75 mL). The organic phase was washed with 5% KHSO$_4$ (2×75 mL) and saturated NaCl solutions, dried (Na$_2$SO$_4$) and evaporated to dryness. The residue was taken up in ethyl acetate (250 mL) and treated with trifluoroacetic acid (0.2 mL). After stirring at room temperature under argon for 18 hours, the mixture was washed with saturated NaHCO$_3$ (3×50 mL) and saturated NaCl solutions, dried (Na$_2$SO$_4$) and concentrated to a small volume (ca 75 mL). Hexane was added to a cloud point, and the product allowed to crystallize at −10° C. The product was collected, washed with hexane and air-dried to give title lactone (8.723 g, 95%) as white crystals, mp 143°–144° C. [alpha]$_D$= +199.7° (c=0.59, CHCl$_3$) TLC (ethyl acetate) R$_f$=0.36.

B.
[1S-[1α(R*),3β,7β,8β(2S*,4S*),8aβ]]-2-Methylbutanoic acid,
3-[(1,1-dimethylethyl)-dimethylsilyl]oxy]-1,2,3,7,8,8a-hexahydro-7methyl-8-[2-(tetrahydro-4-hydroxy-6-oxo-2H-pyran-2-yl)ethyl]-1-naphthalenyl ester To a solution of Part A lactone (3.505 g, 8.63 mmol) in dry tetrahydrofuran (THF) (30 mL) at room temperature under argon was added imidazole (0.665 g, 9.79 mmol), t-butyldimethylsilyl chloride (1.38 g, 9.16 mmol) and 4-(N,N-dimethylamino)pyridine (0.150 g, 1.23 mmol). After stirring at room temperature for 16 hours, additional portions of imidazole (0.120 g, 1.76 mmol) and t-butyldimethylsilyl chloride (0.260 g, 1.72 mmol) were added and stirring continued for an additional 4 hours. The mixture was then diluted with ethyl acetate (100 mL) and washed successively with 5% KHSO$_4$, saturated NaHCO$_3$ and saturated NaCl solutions, dried (Na$_2$SO$_4$) and evaporated to dryness. The crude product was purified by flash chromatography on silica gel (100 g) eluting with ethyl acetate-hexane (1:1) to give title protected lactone (3.706 g, 83%) as a colorless glass. TLC (ethyl acetate) R$_f$=0.56. From the earlier fractions of the chromatography was also isolated the corresponding bis-silyl ether (0.869 g, 16%), TLC (ethyl acetate) R$_f$=0.90.

C.
[1S[1α(R*),3β,4aβ,7β,8β(2S*,4S*),8aβ]-2-Methylbutanoic acid,
decahydro-3-hydroxy-7-methyl-8-[2-(tetrahydro-4-hydroxy-6-oxy-2H-pyran-2-yl)ethyl]-1-naphthalenyl ester To a solution of Part B lactone (5.27 g, 10.1 mmol) in ethyl acetate (120 mL) was added 10% Pt-C (1.10 g) and the resulting mixture hydrogenated at 40 psi (Parr apparatus) for 7 hours. The mixture was filtered through Celite and evaporated to dryness. TLC (ethyl acetate-hexane, 1:1, 2 developments) single product R$_f$=0.34 (R$_f$ of Part B compound, 0.28).

The crude product was taken up in acetonitrile (100 mL) and treated with 48% aqueous HF (1.0 mL, 27 mmol) and stirred at room temperature under argon for 30 minutes. The mixture was then diluted with ethyl acetate (100 mL) and washed with saturated NaHCO$_3$ and saturated NaCl solutions, dried (Na$_2$SO$_4$) and evaporated to dryness. Recrystallization of the crude product from ethyl acetate gave title compound (3.028 g, 73%) as white needles, mp 156°–157° C. [alpha]$_D$= +75.9° (c=0.64, CHCl$_3$). The residue from the mother liquor was purified by flash chromatography on silica gel (80 g) eluting with ethyl acetate-hexane (4:1) to give an additional 0.561 g of title compound (total:3.589 g, 86%) as white crystals after trituration with ethyl acetate-hexane. TLC (ethyl acetate, 2 developments) R$_f$=0.35 (TLC of the crude product also shows traces of the corresponding cis-ring fused product, R$_f$=0.18 and the 1,4-reduction product R$_f$=0.30).

D.
[1S-[1α(R*),3β,4aα,7β,8β(3S*,5R*),8aβ]]-2-Methylbutanoic acid,
8-[7-[[(1,1-dimethylethyl)diphenylsilyl]oxy]-3,5-dihydroxyheptyl]decahydro-3-hydroxy-7-methyl-1-naphthalenyl ester To a solution of Part C compound (2.40 g, 5.85 mmol) in dry THF (100 mL) at −78° C. (dry ice-ethanol bath) under argon was added dropwise via syringe a solution of 1.5M diisobutylaluminum hydride in toluene (12.9 mL, 19.3 mmol). After stirring at −78° C. for 30 minutes, the reaction was quenched by dropwise addition of methanol (3 mL) followed by water (12 mL). The mixture was allowed to warm to room temperature, treated with Celite (12 g) and Na$_2$SO$_4$ (60 gm), stirred for 30 minutes, filtered and evaporated to a white solid. TLC (CH$_3$OH—CH$_2$Cl$_2$; 1:9) R$_f$=0.41 (R$_f$ of Part C compound, 0.47).

The crude lactol was suspended in dry THF (80 mL) and placed in an ice bath. To the resulting mixture was added sodium borohydride (1.20 g, 31.7 mmol) followed by methanol (20 mL) added dropwise. The mixture was allowed to warm to room temperature and stirred for 1 hour. The mixture was again placed in an ice bath and 2N HCl added dropwise until the aqueous phase was acidic and all of the precipitate had dissolved.

The mixture was extracted with ethyl acetate (4×100 mL) and the combined extracts washed with saturated NaCl solution, dried ($Na_2SO_4$) and evaporated to dryness. The crude tetraol (2.51 g, theory 2.42 g) was used directly for the next step without further purification. TLC ($CH_3OH$—$CH_2Cl_2$; 1:9) $R_f$=0.34.

To a solution of the crude tetraol in dry dimethylformamide (30 mL) at room temperature under argon was added imidazole (0.575 g, 8.46 mmol) and t-butyldiphenylsilyl chloride (1.75 mL, 6.73 mmol). After stirring at room temperature for 16 hours, the mixture was diluted with ethyl acetate (100 mL), washed with water (3×75 mL) and saturated NaCl solution, dried ($Na_2SO_4$) and evaporated to dryness. The crude product was purified by flash chromatography on silica gel (80 g) eluting with ethyl acetate-hexane (2:3) to give title compound (2.749 g, 72% overall from Part C compound) as a colorless glass. TLC (acetone-hexane; 1:1), $R_f$=0.60 ($R_f$ of tetraol, 0.18).

E.
[1S-[1α(R*),3β,4aα,7β,8β(4S*,6R*),8aβ]-2-Methylbutanoic acid, 8-[2-[6-[2-[(1,1-dimethylethyl)diphenylsilyl]oxy]ethyl]-2,2dimethyl-1,3-dioxan-4-yl]ethyl]decahydro-3-hydroxy-7-methyl-1-naphthalenyl ester To a solution of Part D compound (3.20 g, 4.91 mmol) in dry acetone (100 mL) at room temperature under argon was added p-toluenesulfonic acid monohydrate (0.050 g, 0.26 mmol). After stirring at room temperature for 6 hours, the mixture was then diluted with ethyl acetate (75 mL) and washed with saturated $NaHCO_3$ (75 mL) and saturated NaCl solutions, dried ($Na_2SO_4$) and evaporated to dryness. The crude product was purified by flash chromatography on silica gel (80 g) eluting with ethyl acetate-hexane (1:4 to 1:1) to give title compound (2.881 g, 85%) as a coloreless glass. TLC (ethyl acetate-hexane; 1:1) $R_f$=0.55. The later fractions from the chromatography yielded 0.151 g of recovered Part D compound, $R_f$=0.14.

F. [4sR-[4a,5α(4R*,6S*),6α,8aβ]]-5-[2-[6-[2-[[(1,1-Dimethylethyl)diphenylsilyl]oxy]ethyl]-2,2-dimethyl-1,3-dioxan-4-yl]ethyl-4a,5,6,7,8,8a-hexahydro-6-methyl-2(1H)-naphthalenone To a solution of Dess-Martin periodinane (2.265 g, 5.34 mmol) in dry $CH_2Cl_2$ (25 mL) at room temperature under argon was added t-butanol (500 μL, 5.30 mmol) and solution of Part E compound (2.840, 4.10 mmol) in $CH_2Cl_2$ (15 mL). After stirring at room temperature for 1 hour, a solution of $Na_2S_2O_3$ (4.50 g. 28.5 mmol) in 1N $NaHCO_3$ (45 mL) was added and the mixture stirred vigorously for 15 minutes. The organic phase was separated, dried ($Na_2SO_4$) and evaporated to dryness. The crude product was purified by filtration through a short column of silica gel (50 g) eluting with ethyl acetate-hexane (1:9); TLC (ethyl acetate-hexane; 35:65) $R_f$=0.40 ($R_f$ of Part E compound; 0.27). The purified product (theory:2.83 g) was taken up in dry toluene (50 mL), treated with diazobicycloundecane (675 μL, 4.51 mmol) and stirred at room temperature for 1 hour. The mixture was washed successively with 5% $KHSO_4$, saturated $NaHCO_3$ and saturated NaCl solutions, dried ($Na_2SO_4$) and evaporated to dryness. The crude product was purified by flash chromatography on silica gel (80 g) eluting with ethyl acetate-hexane (1:9) to give title compound (2.280 g, 94.5%) as a colorless glass. TLC (acetone-hexane; 1:9; 2 developments) $R_f$=0.38 ($R_f$ of β-acyloxy ketone; 0.27).

G.
[4aS-[4aα,5α(4S*,6R*),6α,8aβ]]-5-[2-[6-[2-[[(1,1-Dimethylethyl)diphenylsilyl]oxy]ethyl]-2,2-dimethyl-1,3-dioxan-4-yl]ethyl]octahydro-3,4-dihydroxy-6-methyl-2(1H)-naphthalenone To a solution of Part F compound (2.095 g, 3.56 mmol) in dry pyridine (20 mL) at room temperature under argon wash added a solution of $OsO_4$ (1.00 g, 3.94 mmol) in pyridine (5 mL). After stirring at room temperature for 2 hours, a solution of $NaHSO_3$ (2.00 g, 19.2 mmol) in water (25 mL) was added and the resulting mixture stirred at room temperature for 30 minutes. The mixture was then diluted with ethyl acetate (100 mL) and washed with saturated $NaHSO_3$ (2×75 mL) and saturated NaCl solutions, dried ($Na_2SO_4$) and evaporated to dryness. The crude product was purified by flash chromatography on silica gel (80 g) eluting with ethyl acetate-hexane (1:2) to give title compound (2.173 g, 98%) as a colorless glass (mixture of alpha and beta cis-diols). TLC (ethyl acetate-hexane; 1:1) $R_f$=0.56 (major) and 0.47 (minor) ($R_f$ of Part F compound; 0.80).

H.
[4aS-[4aα,7β,8β(4S*,6R*),8aβ]-8-[2-[6-2-[[(1,1-Dimethylethyl)diphenylsilyloxy]ethyl]-2,2-dimethyl-1,3-dioxan-4-yl]ethyl]octahydro-7-methyl-3H-2-benzopyran-3-one To a solution of Part G compound (1.993 g, 3.21 mmol) in dioxane (24 mL) at room temperature under argon was added a solution of $NaIO_4$ (1.51 g, 7.06 mmol) in water (8 mL). After stirring at room temperature for 16 hours, the mixture was diluted with ethyl acetate (100 mL) and washed with 5% $KHSO_4$, water and saturated NaCl solutions, dried ($Na_2SO_4$) and evaporated to dryness. TLC (ethyl acetate-toluene; 1:4) $R_f$=0.10 ($R_f$ of Part G compound; 0.31 and 0.26).

The crude product was taken up in dry diethyl ether (20 mL), placed in an ice bath and treated with etherial diazomethane in portions until TLC indicated consumption of the starting acid. The mixture was then evaporated to dryness. TLC (ethyl acetate-toluene; 1:4) $R_f$=0.66.

To s solution of the above crude aldehyde in dry THF (20 mL) at 0° C. under argon was added LiAl(O-$C_4H_9)_3$H (1.23 g, 4.83 mmol) in one portion. After stirring at 0° C. for 1 hour, the mixture was partitioned between ethyl acetate-5% $KHSO_4$ (50 mL each). The organic phase was washed with saturated NaCl solution, dried ($Na_2SO_4$) and evaporated to dryness. The crude product was purified by flash chromatography on silica gel (80 g) eluting with ethyl acetate-toluene (5:95) to give title compound (1.551 g, 81.5%) as a colorless glass. TLC (ethyl acetate-toluene; 1:4) $R_f$=0.48.

I.
[1S-[1α,2β(4S*,6R*),3β,6β]-2-[2-[6-[2-[[(1,1-Dimethylethyl)diphenylsilyl]oxy]ethyl]-2,2-dimethyl-1,3-dioxan-4-yl]ethyl]-3-methyl-6-(2-propenyl)cyclohexanemethanol To a solution of Part H compound (0.485 g, 0.819 mmol) in dry toluene (8.0 mL) at −78° C. (dry ice-$C_2H_5OH$ bath) under argon was added dropwise via syringe a solution of 1.5M diisobutylaluminum hydride in toluene (0.57 mL, 0.855 mmol). After stirring at −78° C. for 30 minutes, the reaction was quenched by the addition of silica gel (3 g) followed by water (1.0 mL) and then allowed to warm to room temperature. The mixture was diluted with ethyl acetate (30 mL), filtered and evaporated to dryness to give the crude lactol (0.490 g) as a colorless oil. TLC (ethyl acetate-toluene; 1:4) $R_f=0.35$.

To a suspension of methyltriphenylphosphonium bromide (1.025 g, 2.87 mmol) in dry toluene (12 mL) at 0° C. under argon was added a solution of 1.82M potassium t-amylate (1.35 mL, 2.46 mmol) in toluene dropwise via syringe. After stirring at 0° C. for 1.5 hours, a solution of the above lactol (0.490 g, ca 0.819 mmol) in dry toluene (2 mL) was added in one portion. After stirring at 0° C. for 1 hour and at room temperature for 1.5 hours, the reaction was quenched by the addition of saturated NH$_4$Cl solution (10 mL). The organic phase was separated, washed with 5% KHSO$_4$ and saturated NaCl solutions, dried (Na$_2$SO$_4$) and evaporated to dryness. The crude product was purified by flash chromatography on silica gel (60 g) eluting with ethyl acetate-hexane (1:9) to give title compound (0.446 g, 92%) as a colorless, viscous oil. TLC (ethyl acetate-toluene; 1:4) $R_f=0.51$.

J. [1S-[1α,2β(4S*,6R*),3β,6β]]-2,2-Dimethylbutanoic acid, [2-[2-[6-[2-[[(1,1-dimethylethyl)diphenylsilyl]oxy]ethyl]-2,2-dimethyl-1,3-dioxan-4-yl]ethyl]-3-methyl-6-propylcyclohexyl]methyl ester To a solution of Part I compound (0.446 g, 0.753 mmol) in methanol (8.0 mL) was added 10% Pd-C (0.095 g) and the resulting mixture stirred under a hydrogen atmosphere for 2 hours. The mixture was filtered through Celite and evaporated to dryness. TLC (ethyl acetate-hexane, 3:7) single product $R_f=0.58$ ($R_f$ of Part I compound, 0.55).

To a solution of the above crude product in dry pyridine (4.0 mL) at room temperature under argon was added 2,2-dimethylbutyryl chloride (0.150 g, 1.11 mmole) and 4-(N,N-dimethylamino)pyridine (0.020 g, 0.16 mmol). After stirring at room temperature for 16 hours, the mixture was evaporated to dryness. The residue was taken up in ethyl acetate (50 mL), washed successively with 5% KHSO$_4$, saturated NaHCO$_3$ and saturated NaCl solution, dried (Na$_2$SO$_4$) and evaporated to dryness. The crude product was purified by flash chromatography on silica gel (40 g) eluting with diethyl ether-hexane (5:95) to give title compound (0.476 g, 91% overall from Part I compound) as a colorless, viscous oil. TLC (ethyl acetate-hexane; 1:4) $R_f=0.64$.

K. [1S-[1α,2β2(4S*,6R*),3β,6β]]-2,2-Dimethylbutanoic acid, [2-[2-[6-(2-hydroxyethyl)-2,2-dimethyl-1,3-dioxan-4-yl]ethyl-3-methyl-6-propylcyclohexyl]methyl ester To a solution of Part J compound (0.446 g, 0.644 mmol) in dry THF (6.0 mL) at room temperature under argon was added a solution of 1.0M (n-C$_4$H$_9$)$_4$NF in THF (1.90 mL, 1.90 mmol). After stirring at room temperature for 16 hours, the mixture was then diluted with ethyl acetate (30 mL), washed with 5% KHSO$_4$ and saturated NaCl solutions, dried (Na$_2$SO$_4$) and evaporated to dryness. The crude product was purified by flash chromatography on silica gel (25 g) eluting with ethyl acetate-hexane (1:4) to give title compound (0.247 g, 84%) as a colorless oil. TLC (ethyl acetate-hexane; 1:4) $R_f=0.11$.

L. [1S-[1α,2β(4S*,6S*),3β,6β]]-2,2-Dimethylbutanoic acid, [2-[2-[6-(2-methoxy-2-oxoethyl)-2,2-dimethyl-1,3-dioxan-4-yl]ethyl]-3-methyl-6-propylcyclohexyl]methyl ester To a solution of Dess-Martin periodinane (0.265 g, 0.625 mmol) in dry CH$_2$Cl$_2$ (6 0 mL) at room temperature under argon was added t-butanol (59 μL, 0.63 mmol) and a solution of Part K compound (0.236, 0.520 mmol) in CH$_2$Cl$_2$ (4.0 mL). After stirring at room temperature for 1 hour, a solution of Na$_2$S$_2$O$_3$ (0.690 g, 4.37 mmol) in 1N NaHCO$_3$ (8 mL) was added and the mixture stirred vigorously for 10 minutes. The mixture was diluted with ethyl acetate (50 mL), the organic phase separated and washed with saturated NaHCO$_3$ and saturated NaCl solutions, dried (Na$_2$SO$_4$) and evaporated to dryness. TLC (ethyl acetate-hexane; 3:7) $R_f=0.61$ ($R_f$ of Part K compound; 0.30).

The crude aldehyde was immediately taken up in t-butanol (6.0 mL) and 5% NaH$_2$PO$_4$ (2.0 mL, pH 4.5) and treated with 1.0M KMnO$_4$ solution (3.0 mL, 3.0 mmol). After stirring at room temperature for 5 minutes, the mixture was cooled to 0° C. (ice bath) and the excess KMnO$_4$ quenched with saturated Na$_2$SO$_3$ solution. The mixture was diluted with ethyl acetate (30 mL) and acidified with 10% HCl solution to pH 2. The organic phase was separated, washed with 5% KHSO$_4$ and saturated NaCl solutions, dried (Na$_2$SO$_4$) and evaporated to dryness. TLC (CH$_3$OH-CH$_2$Cl$_2$; 5:95) $R_f=0.11$.

The crude product was taken up in dry diethyl ether (10 mL), placed in an ice bath and treated with etherial diazomethane in portions until TLC indicated consumption of the starting acid. The mixture was then evaporated to dryness. The crude product was purified by flash chromatography on silica gel (20 g) eluting with diethyl ether-hexane (1:9) to give title compound (0.192 g, 77% overall from Part K compound) as a colorless, viscous oil. TLC (CH$_3$OH-CH$_2$Cl$_2$; 5:95) $R_f=0.85$.

M. [1S-[1α,2β(2S*,4S*),3β,6β]-2,2-Dimethylbutanoic acid, 3-methyl-6-propyl-2-[2-(tetrahydro-4-hydroxy-6-oxo-2H-pyran-2-yl)ethyl]cyclohexyl]methyl ester A solution of Part L compound (0.182 g, 0.378 mmol) in a mixture of 48% aqueous HF (0.1 mL) and acetonitrile (10 mL) was stirred at room temperature for 5 hours. The mixture was diluted with ethyl acetate (50 mL) and washed with saturated NaHCO$_3$ and saturated NaCl solutions, dried (Na$_2$SO$_4$) and evaporated to dryness. The crude product was purified by flash chromatography on silica gel (15 g) eluting with ethyl acetate-hexane (3:7 to 1:1) to give title compound (0.152 g, 98%) as a white solid. Trituration of the product with hexane gave pure title compound (0.148 g, 95%) as white crystals, mp 128°-129.5° C. [alpha]$_D$=+34.9° (c=0.54, CHCl$_3$). TLC (ethyl acetate-hexane; 1:1) $R_f=0.16$ ($R_f$ of intermediate dihydroxy-ester; 0.30).

Analysis: Calculated for C$_{24}$H$_{42}$O$_5$: C, 70.20; H, 10.31. Found: C, 70.12; H, 10.25.

EXAMPLE 2

[1S-[1α(βS*,δS*),2β,3α,6α]]-2-[(2,2-Dimethyl-1-oxobutoxy)methyl]-β,δ-dihydroxy-6-methyl-3-propylcyclohexaneheptanoic acid, monolithium salt To a solution of Example 1 lactone (0.145 g, 0.354 mmol) in dioxane (5.0 mL) at room temperature under argon was added 0.1N LiOH solution (3.7 mL, 0.37 mmol). After stirring at room temperature for 2 hours, the mixture was evaporated to dryness. The residue was purified by CHP20 chromatography (10 mL bed volume, 1 inch diameter column) eluting with water followed by $CH_3OH$-water (7:3). The product containing fractions were combined and evaporated to dryness. The residue was taken up in water, filtered and lyophilized to give title compound (0.142 g, 91%) as a fluffy white solid. [alpha]$_D$= +12.1° (c=0.54, $CH_3OH$).
TLC ($CH_3OH$-$CH_3OH$-$CH_2Cl_2$; 1:1:20) $R_f$=0.46.
Analysis: Calculated for $C_{24}H_{43}O_6Li$ 0.5 $H_2O$: C, 65.00; H, 10.00. Found: C, 64.84; H, 10.19.

EXAMPLE 3

[1S-[1α(βS*,δS*),2β,3α,6α]]-2-[[(2,2-Dimethyl-1-oxobutyl)amino]methyl]-β,δ-dihydroxy-6-methyl-3propylcyclohexaneheptanoic acid, monolithium salt

A.

[1S-[1α,2β(4S*,6R*),3β,6β]]-2-[2-[6-[2-[(1,1-Dimethylethyl)diphenylsilyl]oxy]ethyl]-2,2-dimethyl-1,3-dioxan-4-yl]ethyl]-3-methyl-6-propylcyclohexanemethanol To a solution of Example 1 Part I olefin (0.420 g, 0.709 mmol) in methanol (8.0 mL) was added 10% Pd-C (0.085 g) and the resulting mixture stirred under a hydrogen atmosphere for 2 hours. The mixture was filtered through Celite and evaporated to dryness to give title compound (0.414 g, 98%) as a colorless oil. TLC (ethyl acetate (EtOAc)-hexane, 3:7) single product $R_f$=0.58 ($R_f$ of starting olefin, 0.55).

B.

[1S-[1α,2β(4S*,6R*),3β,6β]]-[[2-[2-[6-2-[[(1,1-Dimethylethyl)diphenylsilyl]oxy]ethyl]-2,2-dimethyl-1,3-dioxan-4-yl]-3-methyl-6-propylcyclohexyl]methyl]azide To a solution of Part A compound (0.357 g, 0.601 mmol) in dry methylene chloride (10 mL) at 0° C. (ice bath) under argon was added triethylamine (300 µL, 2.17 mmol) followed by methanesulfonyl chloride (70 µL, 0.90 mmol) added dropwise via microliter syringe. After stirring at 0° C. for 30 minutes, the mixture was diluted with EtOAc (50 mL), washed successively with 5% $KHSO_4$, saturated $NaHCO_3$ and saturated NaCl solutions, dried ($Na_2SO_4$) and evaporated to dryness to give the crude mesylate (0.524 g) as a colorless, viscous oil. TLC (EtOAc-toluene; 15:85) $R_f$=0.67 ($R_f$ of Part A compound, 0.57).

To a solution of the above crude mesylate product in dry N,N-dimethylformamide (6 mL) was added sodium azide (0.200 g, 3.08 mmol) and the resulting mixture heated at 50° C. (bath temperature) for 4 hours. The mixture was diluted with EtOAc (75 mL), washed with water (3×40 mL) and saturated NaCl solution, dried ($Na_2SO_4$) and evaporated to dryness. The crude product was purified by flash chromatography on silica gel (40 g) eluting with diethyl ether-hexane (5:95) to give title azide (0.340 g, 91% overall from Part A compound as a colorless, viscous oil. TLC (EtOAc-hexane; 1:4) $R_f$=0.56 ($R_f$ of mesylate, 0.26).

C.

[1S-[1α,2β(4S*,6R*),3β,6β]]-N-[[2-[2-[6-2-[[(1,1-Dimethylethyl)diphenylsilyl]oxy]ethyl]-2,2-dimethyl-1,3-dioxan-4-yl]ethyl]-3-methyl-6-propylcyclohexyl]methyl]-2,2-dimethylbutanamide To a solution of Part B azide (0.298 g, 0.481 mmol) in a methanol (8.0 mL)-ethanol (6 mL) mixture was added triethylamine (50 µL, 0.36 mmol) and 10% Pd-C (0.095 g) and the resulting mixture stirred under a hydrogen atmosphere for 3 hours. The mixture was filtered through Celite and evaporated to dryness to give the crude amine as a colorless glass. TLC ($CH_3OH$-$CH_2Cl_2$, 5:95) major product $R_f$=0.19.

To a solution of the above crude product in dry pyridine (8.0 mL)-THF (4 mL) at room temperature under argon was added 2,2-dimethylbutyryl chloride (0.130 g, 0.966 mmole) and 4-(N,N-dimethylamino)pyridine (0.020 g, 0.16 mmol). After stirring at room temperature for 2 hours, the mixture was evaporated to dryness. The residue was taken up in EtOAc (50 mL), washed successively with 5% $KHSO_4$, saturated $NaHCO_3$ and saturated NaCl solutions, dried ($Na_2SO_4$) and evaporated to dryness. The crude product was purified by flash chromatography on silica gel (20 g) eluting with EtOAc-hexane (1:9) to give title amide (0.253 g, 76% overall from Part B compound) as a colorless, viscous oil. TLC (EtOAc-hexane; 1:4) $R_f$=0.43.

D.

1S-[1α,2β(4S*,6R*),3β,6β]]-N-[[2-[2-[6-(2-Hydroxyethyl)-2,2-dimethyl-1,3-dioxan-4-yl]ethyl]-3-methyl-6-propylcyclohexyl]methyl]-2,2-dimethylbutanamide To a solution of Part C amide (0.283 g, 0.644 mmol) in dry tetrahydrofuran (THF) (4.0 mL) at room temperature under argon was added a solution of 1.0M (n-$C_4H_9$)$_4$NF in THF (1.20 mL, 1.20 mmol). After stirring at room temperature for 2 hours, the mixture was then diluted with EtOAc (30 mL), washed with 5% $KHSO_4$ and saturated NaCl solutions, dried ($Na_2SO_4$) and evaporated to dryness. The crude product was purified by flash chromatography on silica gel (20 g) eluting with EtOAc-hexane (2:3) to give title amide-alcohol (0.147 g, 79%) as a colorless oil. TLC (EtOAc-hexane; 3:7) $R_f$=0.13.

E.

[1S-[1α,2β(4S*,6R*),3β,6β]]-N-[[2-[2-6-(2-Methoxy-2-oxoethyl)-2,2-dimethyl-1,3-dioxan-4-yl]ethyl]-3-methyl-6-propylcyclohexyl]methyl]-2,2-dimethylbutanamide To a solution of Dess-Martin periodinane (0.165 g, 0.389 mmol) in dry $CH_2Cl_2$ (3.0 mL) at room temperature under argon was added t-butanol (37 µL, 0.39 mmol) and a solution of Part D amidoalcohol (0.147, 0.325 mmol) in $CH_2Cl_2$ (4.0 mL). After stirring at room temperature for 30 minutes, a solution of $Na_2S_2O_3$ (0.430 g, 2.72 mmol) in 1N $NaHCO_3$ (5 mL) was added and the mixture stirred vigorously for 5 minutes. The mixture was diluted with EtOAc (30 mL), the organic phase separated and washed with saturated $NaHCO_3$ and saturated NaCl solutions, dried ($Na_2SO_4$) and evaporated to dryness. TLC (EtOAc-hexane; 3:7) $R_f$=0.43.

The so-formed crude aldehyde was immediately taken up in t-butanol (3.7 mL) and 5% $NaH_2PO_4$ (1.25 mL, pH 4.5) and treated with 1.0M $KMnO_4$ solution (1.85 mL, 1.85 mmol). After stirring at room temperature for 5 minutes, the mixture was cooled to 0° C. (ice bath) and the excess KMnO4 quenched with saturated Na2SO3 solution. The mixture was diluted with EtOAc (30 mL) and acidified with 1N HCl solution to pH 2. The organic phase was separated, washed with 5% KHSO4 and saturated NaCl solutions, dried (Na2SO4) and evaporated to dryness. TLC(CH3OH-CH2Cl2; 5:95) $R_f$=0.25.

The crude product was taken up in dry diethyl ether (10 mL), placed in an ice bath and treated with etherial diazomethane in portions until TLC indicated consumption of the starting acid. The mixture was then evaporated to dryness. The crude product was purified by flash chromatography on silica gel (15 g) eluting with EtOAc-hexane (1:4) to give title ester (0.121 g, 78% overall from Part D compound) as a colorless, viscous oil. TLC (EtOAc-hexane; 2:3) $R_f$=0.41.

F.
[1S-[1α,2β(2S*,4S*),3β,6β]]-N-[[2-[2-(Tetrahydro-4-hydroxy-6-oxo-2H-pyran-2-yl)ethyl-3-methyl-6-propylcyclohexyl]methyl]-2,2-dimethylbutanamide A solution of Part E ester (0.121 g, 0.378 mmol) in a mixture of 48% aqueous HF (0.08 mL) and acetonitrile (8 mL) was stirred at room temperature for 5.5 hours. The mixture was diluted with EtOAc (50 mL) and washed with saturated NaHCO3 and saturated NaCl solutions, dried (Na2SO4) and evaporated to dryness. The crude product was purified by flash chromatography on silica gel (15 g) eluting with EtOAc-hexane (3:2 to 4:1) to give title lactone (0.094 g, 91%) as a white foam. [alpha]$_D$= +25.7° (c=0.54, CHCl3). TLC (EtOAc-hexane; 3:2) $R_f$=0.10 ($R_f$ of intermediate dihydroxy-ester; 0.24).

G.
[1S-[1α(βS*,δS*),2β,3α,6α]-2-[[(2,2-Dimethyl-1-oxobutyl)amino]methyl]-β,δ-dihydroxy-6-methyl-3-propylcyclohexaneheptanoic acid, monolithium salt To a solution of Part F lactone (0.089 g, 0.218 mmol) in dioxane (3.0 mL) at room temperature under argon was added 0.1N LiOH solution (2.4 mL, 0.24 mmol). After stirring at room temperature for 1 hour, the mixture was evaporated to dryness. The residue was purified by CHP20 chromatography (10 mL bed volume, 1 inch diameter column) eluting with water followed by CH3OH-water (7:3). The product containing fractions was combined and evaporated to dryness. The residue was taken up in water, filtered and lyophilized to give title product (0.087 g, 91%) as a fluffy white solid. [alpha]$_D$= +13.8° (c=0.49, CH3OH). TLC (CH3COOH-CH3OH-CH2Cl2; 1:1:20) $R_f$=0.24.

The following additional compounds (Tables 1 and 2) of the invention may be prepared following the procedures described above.

TABLE 1

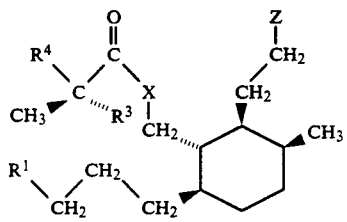

where Z =

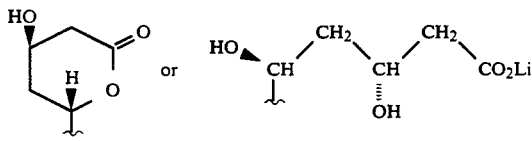

| R¹ | R³ | R⁴ | X |
|---|---|---|---|
| H | H | C2H5 | O |
| C6H5 | CH3 | C2H5 | O |
| p-F—C6H4 | CH3 | C2H5 | O |
| ⟨furan-CH2—⟩ | CH3 | C2H5 | O |
| ⟨pyridin-2-yl⟩ | CH3 | C2H5 | O |
| H | CH3 | ⟨HO-C6H4-CH2—⟩ | O |

TABLE 1-continued

| | | | |
|---|---|---|---|
| p-F—C$_6$H$_4$ | CH$_3$ | 3,5-(HO)$_2$C$_6$H$_3$—CH$_2$— | O |
| H | CH$_3$ | CH$_3$S— | O |
| H | C$_2$H$_5$ | C$_2$H$_5$ | NH |
| CH$_3$ | H | C$_6$H$_5$—CH$_2$— | NCH$_3$ |
| (CH$_3$)$_2$CH | CH$_3$ | 3,5-(HO)$_2$C$_6$H$_3$—CH$_2$— | NH |
| C$_6$H$_5$ | CH$_3$ | C$_2$H$_5$ | NH |
| cyclohexyl | H | C$_2$H$_5$ | NCH$_3$ |
| 2-thienyl | CH$_3$ | 4-HO—C$_6$H$_4$— | NH |
| C$_6$H$_5$ | C$_2$H$_5$ | C$_3$H$_7$ | O |
| cyclopentyl | CH$_3$ | 3-HO—C$_6$H$_4$— | O |
| H | CH$_3$ | CH$_3$ | O |
| H | CH$_3$ | CH$_3$ | NC$_2$H$_5$ |
| CH$_3$O— | CH$_3$ | C$_2$H$_5$ | O |
| C$_6$H$_5$—CH$_2$CH$_2$O— | CH$_3$ | C$_2$H$_5$ | NH |
| 4-CH$_3$—C$_6$H$_4$—CH$_3$ | CH$_3$ | C$_2$H$_5$ | NH |

TABLE 2

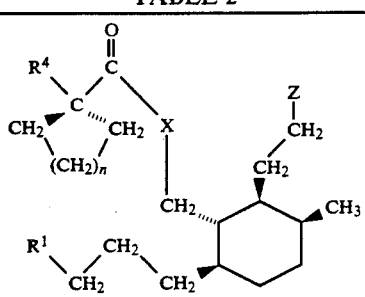

where Z =

HO—CH(—)—CH$_2$—C(=O)—O— (lactone) or HO—CH(—)—CH$_2$—CH(OH)—CH$_2$—CO$_2$Li

| R$^1$ | R$_4$ | n | X |
|---|---|---|---|
| H | C$_2$H$_5$ | 1 | O |
| C$_6$H$_5$ | C$_2$H$_3$ | 3 | O |
| p-F—C$_6$H$_5$ | CH$_3$S— | 2 | O |

TABLE 2-continued

| | | | |
|---|---|---|---|
| H | HO-C6H3(OH)-CH2— (3,5-diOH benzyl) | 1 | O |
| (CH3)2CH | HO-C6H4-CH2— (4-OH benzyl) | 1 | O |
| H | C2H5 | 2 | NH |
| H | C2H5 | 1 | NCH3 |
| CH3 | 3-HO-C6H4-CH2— | 2 | NH |
| H | CH3 | 3 | O |
| furan-2-yl | CH3 | 2 | NH |
| cyclopentyl-CH2— | 4-HO-C6H4-CH2— | 1 | NH |
| cyclopentyl-CH2— | CH3S | 1 | O |
| CH3O | C2H5 | 2 | O |
| C6H5CH2CH2O | C2H5 | 3 | O |

What is claimed is:

1. An intermediate of the structure

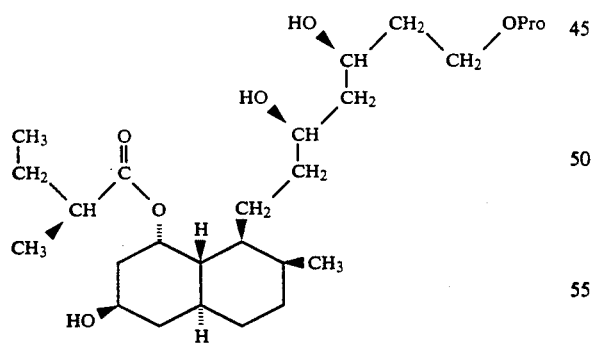

wherein Pro represents a silyl protecting group.

2. An intermediate of the structure

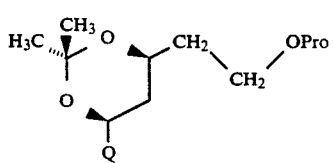

wherein Pro represents a silyl protecting group and Q is

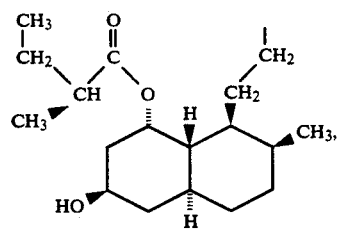

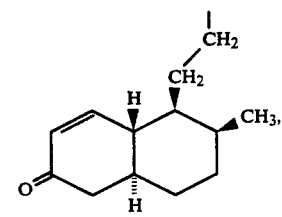

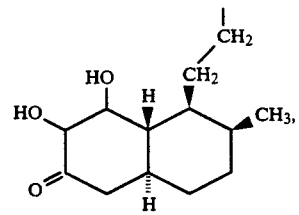

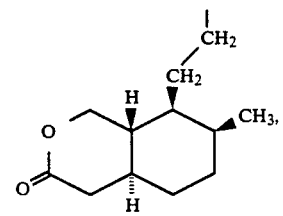

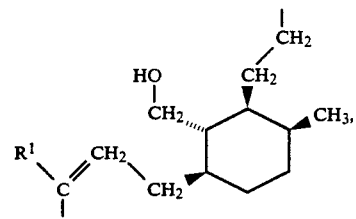

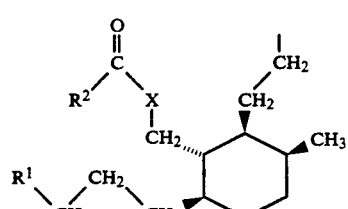

wherein $R^1$ is H, lower alkyl, aryl, lower alkoxy, heteroaryl, aralkyl, heteroaralkyl or heterocyclic; and $R^2$ is lower alkyl, cycloalkyl or aralkyl; and X is O or $NR^5$ wherein $R^5$ is H or alkyl; wherein aryl by itself or as part of another group is a monocyclic or bicyclic aromatic group containing 6 to 10 carbons which may be unsubstituted or substituted with 1 or 2 of lower alkyl, halogen, CF<sub>3</sub>, lower alkoxy, nitro, alkoxy and/or cyano;

heteroaryl by itself or as part of another group is a 5- to 10-membered mono or bicyclic ring containing one or two heteroatoms which are N, S or O;

aralkyl by itself or as part of another group is a lower alkyl group having an aryl substituent;

heteroaralkyl by itself or as part of another group is a heteroaryl linked to an alkylene group;

heterocyclic by itself or as part of another group is a 5- to 10-membered monocyclic or bicyclic ring containing 1 or 2 heteroatoms which are N; N and O; or N and S;

cycloalkyl by itself or as part of another group is a saturated hydrocarbon containing 3 to 12 carbons which is unsubstituted or substituted with 1 or 2 of halogen, lower alkoxy, lower alkyl, hydroxy, lower alkoxycarbonyl, lower alkanoyl, aroyl, aryl, alkylthio, alkylsulfinyl, alkylsulfonyl, cycloalkylthio, cycloalkylsulfinyl, cycloalkylsulfonyl, arylthio and/or oxo.

3. A new intermediate of the structure

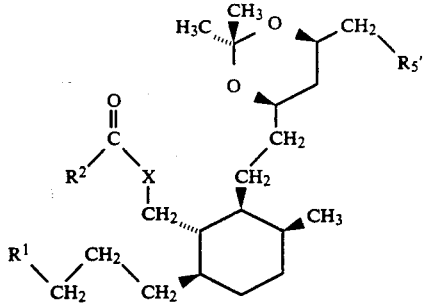

wherein $R^1$ is H, lower alkyl, aryl, lower alkoxy, heteroaryl, aralkyl, heteroaralkyl or heterocyclic; $R^2$ is lower alkyl, cycloalkyl or aralkyl; $R^{5'}$ is $CH_2OH$ or $CO_2$ alkyl; and X is O or $NR^5$ wherein $R^5$ is H or alkyl, wherein aryl by itself or as part of another group is a monocyclic or bicyclic aromatic group containing 6 to 10 carbons which may be unsubstituted or substituted with 1 or 2 of lower alkyl, halogen, $CF_3$, lower alkoxy, nitro, alkoxy and/or cyano;

heteroaryl by itself or as part of another group is a 5- to 10-membered mono or bicyclic ring containing one or two heteratoms which are N, S or O;

aralkyl by itself or as part of another group is a lower alkyl group having an aryl substituent;

heteroaralkyl by itself or as part of another group is a heteroaryl linked to an alkylene group;

heterocyclic by itself or as part of another group is a 5- to 10-membered monocyclic or bicyclic ring containing 1 or 2 heteroatoms which are N; N and O; or N and S;

cycloalkyl by itself or as part of another group is a saturated hydrocarbon containing 3 to 12 carbons which is unsubstituted or substituted with 1 or 2 of halogen, lower alkoxy, lower alkyl, hydroxy, lower alkoxycarbonyl, lower alkanoyl, aroyl, aryl, alkylthio, alkylsulfinyl, alkylsulfonyl, cycloalkylthio, cycloalkylsulfinyl, cycloalkylsulfonyl, arylthio and/or oxo.

* * * * *